US008138164B2

(12) United States Patent
Liverton et al.

(10) Patent No.: US 8,138,164 B2
(45) Date of Patent: Mar. 20, 2012

(54) HCV NS3 PROTEASE INHIBITORS

(75) Inventors: Nigel J. Liverton, Harleysville, PA (US); Vincenzo Summa, Rome (IT); Joseph P. Vacca, Telford, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 368 days.

(21) Appl. No.: 12/446,341

(22) PCT Filed: Oct. 19, 2007

(86) PCT No.: PCT/US2007/022342

§ 371 (c)(1), (2), (4) Date: Apr. 20, 2009

(87) PCT Pub. No.: WO2008/051475

PCT Pub. Date: May 2, 2008

(65) Prior Publication Data

US 2010/0317623 A1 Dec. 16, 2010

Related U.S. Application Data

(60) Provisional application No. 60/854,017, filed on Oct. 24, 2006.

(51) Int. Cl.
*A61K 31/675* (2006.01)
*C07D 498/14* (2006.01)
*A61P 31/14* (2006.01)

(52) U.S. Cl. ................................ 514/81; 514/2; 540/455

(58) Field of Classification Search .................. 514/181, 514/2; 540/455

See application file for complete search history.

(56) References Cited

U.S. PATENT DOCUMENTS

| | | | |
|---|---|---|---|
| 3,480,613 | A | 11/1969 | Walton |
| 6,323,180 | B1 | 11/2001 | Llinas-Brunet et al. |
| 6,608,027 | B1 | 8/2003 | Tzantrizos et al. |
| 6,777,395 | B2 | 8/2004 | Bhat et al. |
| 6,955,174 | B2 | 10/2005 | Friedrichs et al. |
| 7,470,664 | B2 | 12/2008 | Holloway et al. |
| 2002/0019363 | A1 | 2/2002 | Ismaili et al. |
| 2002/0107138 | A1 | 8/2002 | Hoveyda et al. |
| 2003/0236216 | A1 | 12/2003 | Devos et al. |
| 2004/0006007 | A1 | 1/2004 | Gosselin et al. |
| 2004/0063658 | A1 | 4/2004 | Roberts et al. |
| 2004/0067901 | A1 | 4/2004 | Bhat et al. |
| 2004/0229776 | A1 | 11/2004 | Chen et al. |
| 2004/0229818 | A1 | 11/2004 | Llinas-Brunet et al. |
| 2004/0254159 | A1 | 12/2004 | Hasvold et al. |
| 2004/0266668 | A1 | 12/2004 | Nakajima et al. |
| 2005/0020503 | A1 | 1/2005 | Llinas-Brunet et al. |
| 2005/0038240 | A1 | 2/2005 | Connolly et al. |
| 2006/0257980 | A1 | 11/2006 | Li |
| 2007/0027071 | A1 | 2/2007 | Holloway et al. |

FOREIGN PATENT DOCUMENTS

| | | | |
|---|---|---|---|
| EP | 1719773 | A1 | 11/2006 |
| GB | 2337262 | A | 11/1999 |
| GB | 2430621 | A | 4/2007 |
| WO | 97/41211 | A1 | 11/1997 |
| WO | 98/22496 | A2 | 5/1998 |
| WO | 98/46630 | A1 | 10/1998 |
| WO | 99/07733 | A2 | 2/1999 |
| WO | 99/07734 | A2 | 2/1999 |
| WO | 99/38888 | A1 | 8/1999 |
| WO | 99/43691 | A1 | 9/1999 |
| WO | 99/50230 | A1 | 10/1999 |
| WO | 99/64442 | A1 | 12/1999 |
| WO | 00/09543 | A2 | 2/2000 |
| WO | 00/09546 | A2 | 2/2000 |
| WO | 00/25780 | A1 | 5/2000 |
| WO | 00/59929 | A1 | 10/2000 |
| WO | 01/00622 | A1 | 1/2001 |
| WO | 01/47883 | A1 | 7/2001 |
| WO | 01/60379 | A1 | 8/2001 |

(Continued)

OTHER PUBLICATIONS

Youla S. Tsantrizos, The Design of a Potent Inhibitor of the Hepatitis C Virus NS3 Protease: BILN 2061—From the NMR Tube to the Clinic, 76 Biopolymers (Peptide Science) 309-323 (2004).

(Continued)

*Primary Examiner* — San-Ming Hui
*Assistant Examiner* — Kathrien Cruz
(74) *Attorney, Agent, or Firm* — Julie M. Lake; Sheldon O. Heber

(57) ABSTRACT

The present invention relates to macrocyclic compounds of formula (I) that are useful as inhibitors of the hepatitis C virus (HCV) NS3 protease, their synthesis, and their use for treating or preventing HCV infections.

(I)

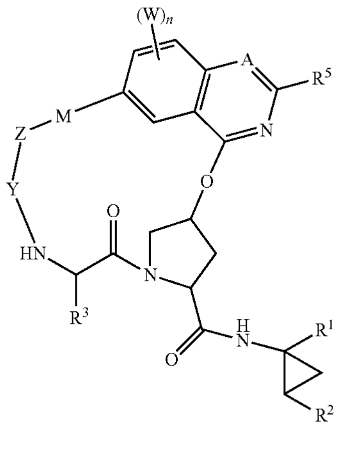

21 Claims, No Drawings

FOREIGN PATENT DOCUMENTS

| | | | |
|---|---|---|---|
| WO | 01/68663 | A1 | 9/2001 |
| WO | 01/77091 | A2 | 10/2001 |
| WO | 01/77113 | A2 | 10/2001 |
| WO | 01/79246 | A2 | 10/2001 |
| WO | 01/90121 | A2 | 11/2001 |
| WO | 01/92282 | A2 | 12/2001 |
| WO | 02/04425 | A1 | 1/2002 |
| WO | 02/06246 | A1 | 1/2002 |
| WO | 02/18404 | A2 | 3/2002 |
| WO | 02/20497 | A1 | 3/2002 |
| WO | 02/32920 | A2 | 4/2002 |
| WO | 02/48116 | A2 | 6/2002 |
| WO | 02/48165 | A2 | 6/2002 |
| WO | 02/48172 | A2 | 6/2002 |
| WO | 02/051425 | A1 | 7/2002 |
| WO | 02/057287 | A2 | 7/2002 |
| WO | 02/057425 | A2 | 7/2002 |
| WO | 02/100415 | A2 | 12/2002 |
| WO | 03/015755 | A1 | 2/2003 |
| WO | 03/026589 | A2 | 4/2003 |
| WO | 03/026675 | A1 | 4/2003 |
| WO | 03/062192 | A1 | 7/2003 |
| WO | 03/062211 | A1 | 7/2003 |
| WO | 03/064455 | A2 | 8/2003 |
| WO | 03/068244 | A1 | 8/2003 |
| WO | 03/093290 | A2 | 11/2003 |
| WO | 03/099274 | A1 | 12/2003 |
| WO | 2004/000858 | A2 | 12/2003 |
| WO | 2004/002422 | A2 | 1/2004 |
| WO | 2004/002999 | A2 | 1/2004 |
| WO | 2004/003000 | A2 | 1/2004 |
| WO | 2004/003138 | A2 | 1/2004 |
| WO | 2004/007512 | A2 | 1/2004 |
| WO | 2004/011478 | A2 | 2/2004 |
| WO | 2004/013300 | A2 | 2/2004 |
| WO | 2004/028481 | A2 | 4/2004 |
| WO | 2004/041201 | A2 | 5/2004 |
| WO | 2004/087714 | A1 | 10/2004 |
| WO | 2004/093915 | A1 | 11/2004 |
| WO | 2004/103996 | A1 | 12/2004 |
| WO | 2004/110442 | A1 | 12/2004 |
| WO | 2005/003147 | A2 | 1/2005 |
| WO | 2005/016927 | A1 | 2/2005 |
| WO | 2005/023819 | A1 | 3/2005 |
| WO | 2005/034941 | A1 | 4/2005 |
| WO | 2005/046712 | A1 | 5/2005 |
| WO | 2005/070955 | A1 | 8/2005 |
| WO | 2005/080399 | A1 | 9/2005 |
| WO | 2006/008556 | A1 | 1/2006 |
| WO | 2006/020082 | A1 | 2/2006 |
| WO | 2006/021341 | A1 | 3/2006 |
| WO | 2006/027628 | A2 | 3/2006 |
| WO | 2006/029912 | A1 | 3/2006 |
| WO | 2006/046030 | A1 | 5/2006 |
| WO | 2006/046039 | A2 | 5/2006 |
| WO | 2006/119061 | A2 | 11/2006 |
| WO | 2006/119975 | A1 | 11/2006 |
| WO | 2007/015787 | A1 | 2/2007 |
| WO | 2007/015855 | A1 | 2/2007 |
| WO | 2007/016441 | A1 | 2/2007 |
| WO | 2007/028789 | A1 | 3/2007 |
| WO | 2007/029029 | A2 | 3/2007 |
| WO | 2007/131966 | A1 | 11/2007 |
| WO | 2007/145894 | A2 | 12/2007 |
| WO | 2007/148135 | A1 | 12/2007 |
| WO | 2008/051475 | A2 | 5/2008 |
| WO | 2008/051477 | A2 | 5/2008 |
| WO | 2008/051514 | A2 | 5/2008 |
| WO | 2008/057028 | A1 | 5/2008 |
| WO | 2008/057208 | A2 | 5/2008 |
| WO | 2008/057209 | A1 | 5/2008 |
| WO | 2008/112108 | A1 | 9/2008 |
| WO | 2009/005687 | A1 | 1/2009 |
| WO | 2009/010804 | A1 | 1/2009 |
| WO | 2009/064955 | A1 | 5/2009 |
| WO | 2009/064975 | A1 | 5/2009 |

OTHER PUBLICATIONS

PCT/US2007/22342, International Search Report (Nov. 20, 2008).

PCT/US2007/22342, International Preliminary Examination Report & Written Opinion of the International Searching Authority (Apr. 28, 2009).

Youwei Yan et al., Complex of NS3 protease and NS4A peptide of BK strain hepatitis C virus: A 2.2 Angstrom resolution structure in a hexagonal crystal form, 7 Protein Science 837 (1998).

Brian W Dymock et al., "Novel Approaches to the Treatment of Hepatitis C Virus Infection," 11 Antiviral Chemistry & Chemotherapy 79-96 (2000).

Hugo R. Rosen & David R. Gretch, "Hepatitis C virus: current understanding and prospects for future therapies," 5 Molec. Med. Today 393-99 (1999).

Darius Moradpour & Hubert E Blum, "Current and evolving therapies for hepatitis C," 11 Euro. J. Gastroenterol. Hepatol. 1189-1202 (1999).

Ralf Bartenschlager, "Candidate Targets for Hepatitis C Virus-Specific Antiviral Therapy," 40(5-6) Intervirology 378-93 (1997).

Georg M. Lauer & Bruce D. Walker, "Hepatitis C Virus Infection," 345(1) N. Engl. J. Med. 41-52 (2001); correction: 345(19) N. Engl. J. Med. 1425-26 (2001).

Brain W. Dymock, "Emerging therapies for hepatitis C virus infection," 6 Emerging Drugs 13-42 (2001).

Charlene Crabb, Infectious Diseases. "Hard-Won Advances Spark Excitement about Hepatitis C," Science 506-507 (2001).

Rogers E. Harry-O'Kuru et al., "A Short, Flexible Route toward 2'-C-Branched Ribonucleosides," 62 J. Org. Chem. 1754-59 (1997).

Michael S. Wolfe & Rogers E. Harry-O'Kuru, "A Concise Synthesis of 2'-C-Methylribonucleosides," 36(42) Tetrahedron Letters 7611-14 (1995).

Scott J. Miller et al., "Application of Ring-Closing Metathesis to the Synthesis of Rigidified Amino Acids and Peptides," 118 J. Am. Chem. Soc. 9606-14 (1996).

Jason S. Kingsbury et al., "A Recyclable Ru-Based Metathesis Catalyst," 121 J. Am. Chem. Soc. 791-99 (1999).

Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).

Alois Furstner et al., "Total Synthesis and Structural Refinement of the Cyclic Tripyrrole Pigment Nonylprodigiosin," 64 J. Org. Chem. 8275-80 (1999).

Tina M. Trnka & Robert H. Grubbs, "The Development of L2X2R-CHR Olefin Metathesis Catalysts: An Organometallic Success Story," 34 Acc. Chem. Res. 18-29 (2001).

A. Srikrishna et al., "Enantiospecific Construction of the BC-ring System of Taxanes," 45 Tetrahedron Letters 2939-42 (2004).

Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).

Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).

Paola Conti et al., "Chemoenzymatic Synthesis of the Enantiomers of Desoxymuscarine," 9 Tetrahedron: Asymmetry 657-65 (1998).

Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).

D. Becker & N. Haddad, "Steric Effects in Intramolecular [2+2] Photocycloaddition of C=C Double Bonds to Cyclohexenones," 49(4) Tetrahedron 947-64 (1993).

Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).

Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).

Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).
Herbert O. House et al., "Cyclization of Unsaturated Hydroxylamine Derivatives," 41(5) J. Org. Chem. 855-63 (1976).
Theophil Eicher et al., "Bryophyte Constituents; 7: New Synthesis of (+)-Rosmarinic Acid and Related Compounds," Synthesis 755-62 (Jun. 1996).
Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).
Marc-Andre Poupart et al., "Solid-Phase Synthesis of Peptidomimetic Inhibitors for the Hepatitis C Virus NS3 Protease," 66(14) J. Org. Chem. 4743-51 (2001).
Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).
Anthony C. Allison & Elsie M. Eugui, "Immunosuppressive and other anti-rheumatic activities of mycophenolate mofetil," 44 Agents and Actions Supplements 165-88 (1993).
Joel Kirschbaum, "Amantadine," 12 Profiles of Drug Substances, Excipients and Related Methodology 1-36 (1983).
T. K. Chakaborty et al., "Alpha-Phenylglycinol as chiral auxilliary in diastereoselective Strecker synthesis of alpha-amino acids," 51(33) Tetrahedron 9179-90 (1995).
W. Clark Still et al., "Rapid Chromatographic Technique for Preparative Separations with Moderate Resolution," 43(14) J. Org. Chem. 2923-25 (1978).
Michael D. Cooke et al., :The occurrence of a hydride shift in the aromatization of 1,4-epoxy-1,2-dihydronaphthalenes, 11 J. Chem. Soc. Perkin Trans. I: Phys. Org. Chem. 1377 (1984).
Paul Aeberli et al., "Neuropharmacological investigation of N-benzylsulfamides," 10(4) J. Med. Chem. 636-42 (1967).
Nathalie Goudreau & Montse Llinas-Brunet, "The Therapeutic Potential of NS3 Protease Inhibitors in HCV Infection," 14(9) Expert Opinion 1129-44 (2005).
Volker Lohmann et al., "Selective Stimulation of Hepatitis C Virus and Pestivirus NS5B RNA Polymerase Activity by GTP," 274(16) J. Bio. Chem. 10807-15 (1999).
V. Lohmann et al., "Replication of Subgenomic Hepatitis C Virus RNAs in a Hepatoma Cell Line," 285 Science 110-13 (1999).
Kevin X. Chen et al. "Novel Potent Hepatitis C Virus NS3 Serine Protease Inhibitors Derived from Proline-Based Macrocycles," 49 J. Med. Chem. 995-1005 (2006).
Yuri Goldberg et al., "Highly regioselective bromination of 2,3-dimethylanisole with N-bromosuccinimide," 57 J. Org. Chem. 6374-76 (1992).
Manfred Schlosser et al., "8-Methoxyisoquinoline derivatives through ortho-selective metallation of 2-(3-methoxyphenyl)ethylamines," 32(17) Tetrahedron Letters 1965-66 (1991).
Angela Casini et al., "Carbonic Anhydrase inhibitors inhibition of cytosolic isozymes I and II with sulfamide derivatives," 13(5) Bioorg. Med. Chem. Lett. 837-40 (2003).
Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).
Duane E. Rudisill & J. K. Stille, "Palladium-catalyzed synthesis of 2-substituted indoles," 54(25) J. Org. Chem. 5856-66 (2002).
Makoto Satoh et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).
Yuusaku Yokoyama et al., "Palladium-Catalyzed Reaction of 3-Bromoindole Derivative with Allyl Esters in the Presence of Hexa-n-butyldistannane," 31(8) Heterocycles 1505-11 (1990).
Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (200.8).
John A. McCauley et al., "Bismacrocyclic Inhibitors of Hepatitis C NS31/4a Protease," 47 Angew. Chem. Int. Ed. 9104-07 (2008).
Ashok Arasappan et al., "P2-P4 Macrocyclic inhibitors of hepatitis C virus NS3-4A serine protease," 16 Bioorganic & Medicinal Chemistry Letters 3960-65 (2006).

HCV NS3 PROTEASE INHIBITORS

CROSS-REFERENCE TO RELATED APPLICATIONS

This application is a National Stage application of International Patent Application No. PCT/US2007/022342, filed Oct. 19, 2007. This application also claims priority to U.S. Provisional Patent Application No. 60/854,017, filed Oct. 24, 2006.

FIELD OF THE INVENTION

The present invention relates to macrocyclic compounds that are useful as inhibitors of the hepatitis C virus (HCV) NS3 protease, their synthesis, and their use for treating or preventing HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 3.9 million infected people in the United States alone, according to the U.S. Center for Disease Control, roughly five times the number of people infected with the human immunodeficiency virus (HIV). According to the World Health Organization, there are more than 170 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring.

Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The current state of the art in the treatment of HCV infection has been discussed in the following references: B. Dymock, et al., "Novel approaches to the treatment of hepatitis C virus infection," *Antiviral Chemistry & Chemotherapy,* 11: 79-96 (2000); H. Rosen, et al., "Hepatitis C virus: current understanding and prospects for future therapies," *Molecular Medicine Today,* 5: 393-399 (1999); D. Moradpour, et al., "Current and evolving therapies for hepatitis C," *European J. Gastroenterol. Hepatol.,* 11: 1189-1202 (1999); R. Bartenschlager, "Candidate Targets for Hepatitis C Virus-Specific Antiviral Therapy," *Intervirology,* 40: 378-393 (1997); G. M. Lauer and B. D. Walker, "Hepatitis C Virus Infection," *N. Engl. J. Med.,* 345: 41-52 (2001); B. W. Dymock, "Emerging therapies for hepatitis C virus infection," *Emerging Drugs,* 6: 13-42 (2001); and C. Crabb, "Hard-Won Advances Spark Excitement about Hepatitis C," *Science:* 506-507 (2001).

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein, and is considered a prime drug target since it is responsible for an intramolecular cleavage at the NS3/4A site and for downstream intermolecular processing at the NS4A/4B, NS4B/5A and NS5A/5B junctions. Previous research has identified classes of peptides, such as hexapeptides as well as tripeptides discussed in U.S. Patent Application Publications US 2005/0020503, US 2004/0229818, and US 2004/00229776, showing degrees of activity in inhibiting the NS3 protease. The aim of the present invention is to provide further compounds which exhibit activity against the HCV NS3 protease.

SUMMARY OF THE INVENTION

The present invention relates to novel macrocyclic compounds of formula (I) and/or pharmaceutically acceptable salts and/or hydrates thereof. These compounds are useful in the inhibition of HCV (hepatitis C virus) NS3 (non-structural 3) protease, the prevention or treatment of one or more of the symptoms of HCV infection, either as compounds or their pharmaceutically acceptable salts and/or hydrates (when appropriate), or as pharmaceutical composition ingredients, whether or not in combination with other HCV antivirals, anti-infectives, immunomodulators, antibiotics or vaccines. More particularly, the present invention relates to a compound of formula (I)

(I)

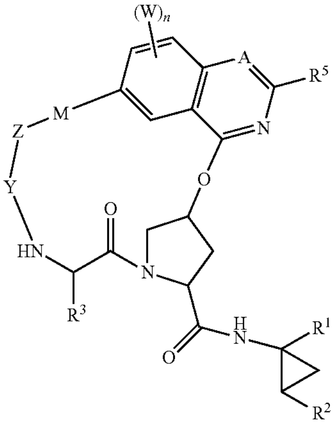

or a pharmaceutically acceptable salt and/or hydrate thereof, wherein:

n is 1 or 2;

$R^1$ is —$CONHR^6$, —$CONHP(O)R^{11}R^{12}$, or —$P(O)R^{11}R^{12}$;

$R^2$ is $C_1$-$C_6$ alkyl, $C_2$-$C_6$ alkenyl or $C_3$-$C_8$ cycloalkyl, wherein said alkyl, alkenyl or cycloalkyl is optionally substituted with 1 to 3 halo;

$R^3$ is $C_1$-$C_8$ alkyl, $C_3$-$C_8$ cycloalkyl, $C_3$-$C_8$ cycloalkyl($C_1$-$C_8$)alkyl, aryl($C_1$-$C_8$)alkyl, or Het, wherein aryl is phenyl or naphthyl and said alkyl, cycloalkyl, or aryl is optionally substituted with 1 to 3 substituents selected from the group consisting of halo, —$OR^{10}$, —$SR^{10}$, —$N(R^{10})_2$, —$N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2(C_1$-$C_6$ alkyl), —$S(O)(C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, —$C(O)R^{10}$, and —$CON(R^{10})_2$; Het is a 5- to 6-membered saturated cyclic ring having 1, 2 or 3 heteroatoms selected from N, O and S, wherein said ring is optionally substituted with 1 to 3 substituents selected from the group consisting of halo, —$OR^{10}$, —$SR^{10}$, —$N(R^{10})_2$, —$N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2(C_1$-$C_6$ alkyl), —$S(O)(C_1$-$C_6$ alkyl), $—NR^{10}SO_2R^6$, $—SO_2N(R^6)_2$, $—NHCOOR^6$, $—NHCOR^6$, $—NHCONHR^6$, $—CO_2R^{10}$, $—C(O)R^{10}$, and $—CON(R^{10})_2$;

$R^4$ is H, $C_1$-$C_8$ alkyl, $C_3$-$C_8$ cycloalkyl($C_1$-$C_8$)alkyl, or aryl ($C_1$-$C_8$)alkyl; wherein aryl is phenyl or naphthyl and said alkyl, cycloalkyl, or aryl is optionally substituted with 1 to 3 substituents selected from the group consisting of halo, $—OR^{10}$, $—SR^{10}$, $—N(R^{10})_2$, $—N(C_1$-$C_6$ alkyl)O($C_1$-$C_6$ alkyl), $C_1$-$C_6$ alkyl, $C_1$-$C_6$ haloalkyl, halo($C_1$-$C_6$ alkoxy), $—NO_2$, —CN, $—CF_3$, $—SO_2(C_1$-$C_6$ alkyl), $—S(O)(C_1$-$C_6$ alkyl), $—NR^{10}SO_2R^6$, $—SO_2N(R^6)_2$, $—NHCOOR^6$, $—NHCOR^6$, $—NHCONHR^6$, $—CO_2R^{10}$, $—C(O)R^{10}$, and $—CON(R^{10})_2$;

$R^5$ is H, halo, —OH, $C_1$-$C_6$ alkoxy, $C_1$-$C_6$ alkyl, —CN, $—CF_3$, $—SR^{10}$, $—SO_2(C_1$-$C_6$ alkyl), $C_3$-$C_8$ cycloalkyl, $C_3$-$C_8$ cycloalkoxy, $C_1$-$C_6$ haloalkyl, $—N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, $—OR^{10}$, $—SR^{10}$, $—N(R^7)_2$, $—N(C_1$-$C_6$ alkyl)O($C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, $—NO_2$, —CN, $—CF_3$, $—SO_2(C_1$-$C_6$ alkyl), $—NR^{10}SO_2R^6$, $—SO_2N(R^6)_2$, $—S(O)(C_1$-$C_6$ alkyl), $—NHCOOR^6$, $—NHCOR^6$, $—NHCONHR^6$, $—CO_2R^{10}$, $C(O)R^{10}$, and $—CON(R^{10})_2$; wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^6$ is $C_1$-$C_8$ alkyl, $C_3$-$C_8$ cycloalkyl, $C_3$-$C_8$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W' substituents or aryl is substituted by $—P(O)R^{11}R^{12}$; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Y is —C(═O)—, $—SO_2—$, or —C(═N—CN)—;

Z is $—C(R^{10})_2—$, —O—, or $—N(R^4)—$;

M is $C_1$-$C_{12}$ alkylene or $C_2$-$C_{12}$ alkenylene or $C_2$-$C_{12}$ alkynylene, wherein said alkylene or alkenylene is optionally substituted with 1, 2 or 3 substituents selected from the group consisting of $C_1$-$C_8$ alkyl, $C_3$-$C_8$ cycloalkyl($C_1$-$C_8$ alkyl), and aryl($C_1$-$C_8$ alkyl); wherein 2 substituents on adjacent carbon atoms of M are optionally taken together to form a 3- to 6-membered cyclic ring containing 0 to 3 heteroatoms selected from N, O and S, or 2 substituents on the same carbon atom of M are optionally taken together to form a 3- to 6-membered cyclic ring containing 0 to 3 heteroatoms selected from N, O and S;

A is $—C(R^{16})—$ or —N—;

when $R^5$ is other than H, $R^{16}$ is H, $C_1$-$C_6$ alkyl, halo, $—OR^{10}$, $—SR^{10}$, or $—N(R^{10})_2$;

when $R^5$ is H, $R^{16}$ is H, $C_1$-$C_6$ alkyl, halo, —OH, $C_1$-$C_6$ alkoxy, —CN, $—CF_3$, $—SR^{10}$, $—SO_2(C_1$-$C_6$ alkyl), $C_3$-$C_8$ cycloalkyl, $C_3$-$C_8$ cycloalkoxy, $C_1$-$C_6$ haloalkyl, $—N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, $—OR^{10}$, $—SR^{10}$, $—N(R^7)_2$, $—N(C_1$-$C_6$ alkyl)O($C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, $—NO_2$, —CN, $—CF_3$, $—SO_2(C_1$-$C_6$ alkyl), $—NR^{10}SO_2R^6$, $—SO_2N(R^6)_2$, $—S(O)(C_1$-$C_6$ alkyl), $—NHCOOR^6$, $—NHCOR^6$, $—NHCONHR^6$, $—CO_2R^{10}$, $—C(O)R^{10}$, and $—CON(R^{10})_2$; wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

or $R^5$ and $R^{16}$ are optionally taken together to form a 5- to 6-membered saturated, unsaturated non-aromatic, or aromatic cyclic ring having 0 to 2 heteroatoms selected from N, O and S;

each $R^7$ is independently H, $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W' substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently H, halo, $—OR^7$, $C_1$-$C_6$ alkyl, —CN, $—CF_3$, $—NO_2$, $—SR^7$, $—CO_2R^7$, $—CON(R^7)_2$, $—C(O)R^7$, $—N(R^{10})C(O)R^7$, $—SO_2(C_1$-$C_6$ alkyl), $—S(O)(C_1$-$C_6$ alkyl), $C_3$-$C_8$ cycloalkyl, $C_3$-$C_8$ cycloalkoxy, $C_1$-$C_6$ haloalkyl, $—N(R^7)_2$, $—N(C_1$-$C_6$ alkyl)O($C_1$-$C_6$ alkyl), halo($C_1$-$C_6$ alkoxy), $—NR^{10}SO_2R^7$, $—SO_2N(R^7)_2$, $—NHCOOR^7$, $—NHCONHR^7$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein 2 adjacent W moieties are optionally taken together with the atoms to which they are attached to form a 5- to 6-membered saturated, unsaturated non-aromatic, or aromatic cyclic ring having 0 to 2 heteroatoms selected from N, O and S;

each W' is independently H, halo, $—OR^{10}$, $C_1$-$C_6$ alkyl, —CN, $—CF_3$, $—NO_2$, $—SR^{10}$, $—CO_2R^{10}$, $—CON(R^{10})_2$, $—C(O)R^{10}$, $—N(R^{10})C(O)R^{10}$, $—SO_2(C_1$-$C_6$ alkyl), $—S(O)(C_1$-$C_6$ alkyl), $C_3$-$C_8$ cycloalkyl, $C_3$-$C_8$ cycloalkoxy, $C_1$-$C_6$ haloalkyl, $—N(R^{10})_2$, $—N(C_1$-$C_6$ alkyl)O($C_1$-$C_6$ alkyl), halo($C_1$-$C_6$ alkoxy), $—NR^{10}SO_2R^{10}$, $—SO_2N(R^{10})_2$, $—NHCOOR^{10}$, $—NHCONHR^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein 2 adjacent W' moieties are optionally taken together with the atoms to which they are attached to form a 5- to 6-membered saturated, unsaturated non-aromatic, or aromatic cyclic ring having 0 to 2 heteroatoms selected from N, O and S;

each $R^{10}$ is independently H or $C_1$-$C_6$ alkyl;

each $R^{11}$ is independently $C_1$-$C_6$ alkyl, —$OR^{13}$, —$N(R^{10})$—V—$CO_2R^{10}$, —O—V—$CO_2R^{10}$, —S—V—$CO_2R^{10}$, —$N(R^{10})(R^{13})$, $R^{14}$, or —$N(R^{10})SO_2R^6$;

each $R^{12}$ is independently —$OR^{13}$, —$N(R^{10})$—V—$CO_2R^{10}$, —O—V—$CO_2R^{10}$, —S—V—$CO_2R^{10}$, or —$N(R^{10})(R^{13})$;

or $R^{11}$ and $R^{12}$ are optionally taken together, with the phosphorus atom to which they are attached, to form a 5- to 7-membered monocyclic ring;

each V is independently —$CH(R^{15})$ or $C_1$-$C_4$ alkylene-$CH(R^{15})$;

each $R^{13}$ is independently H, $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of aryl, aryl($C_1$-$C_4$ alkyl), $C_3$-$C_8$ cycloalkyl, $C_3$-$C_8$ cycloalkyl($C_1$-$C_4$ alkyl), heteroaryl, heteroaryl($C_1$-$C_4$ alkyl), heterocyclyl, heterocyclyl($C_1$-$C_4$ alkyl), $C_1$-$C_6$ alkyl, halo, —$OC(O)OR^6$, —$OC(O)R^6$, —$OR^{10}$, —$SR^{10}$, —$N(R^{10})_2$, —$C(O)R^{10}$, —$NO_2$, —CN, —$CF_3$, —$SO_2$($C_1$-$C_6$ alkyl), —S(O)($C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, and —$C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^{14}$ is $C_1$-$C_6$ alkyl, $C_2$-$C_6$ alkenyl, aryl or heteroaryl, wherein aryl is phenyl or naphthyl, and heteroaryl is independently a 5- or 6-membered aromatic ring having 1, 2 or 3 heteroatoms selected from N, O and S, attached through a ring carbon or nitrogen, and wherein said aryl or heteroaryl is optionally substituted with 1 to 2 substituents selected from the group consisting of $C_1$-$C_6$ alkyl, halo, —$OC(O)OR^6$, —$OC(O)R^6$, —$OR^{10}$, —$SR^{10}$, —$N(R^{10})_2$, —$C(O)R^{10}$, —$NO_2$, —CN, —$CF_3$, —$SO_2$($C_1$-$C_6$ alkyl), —S(O)($C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, and —$C(O)N(R^{10})_2$; and each $R_{15}$ is independently $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of $C_1$-$C_6$ alkyl, halo, —$OC(O)OR^6$, —$OC(O)R^6$, —$OR^{10}$, —$SR^{10}$, —$N(R^{10})_2$, —$C(O)R^{10}$, —$NO_2$, —CN, —$CF_3$, —$SO_2$($C_1$-$C_6$ alkyl), —S(O)($C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, and —$C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S.

In one embodiment of the invention, n is 1, and all other variables are as previously defined.

In another embodiment of the invention, $R^1$ is —$P(O)R^{11}R^{12}$, and all other variables are as previously defined. In a preferred group of this embodiment, $R^{11}$ is independently $C_1$-$C_6$ alkyl, or —$OR^{13}$, and $R^{12}$ is independently —$OR^{13}$, and all other variables are as previously defined. In a more preferred group of this embodiment, $R^{13}$ is H or $C_1$-$C_6$ alkyl, and all other variables are as previously defined. In an even more preferred embodiment of the invention, R11 is selected from the group consisting of —$OCH_2CH_3$, —$CH_3$, and —OH, and $R^{12}$ is —OH, and all other variables are as previously defined.

In another embodiment of the invention, $R^2$ is $C_1$-$C_6$ alkyl or $C_2$-$C_6$ alkenyl, and all other variables are as previously defined. In a more preferred group of this embodiment, $R^2$ is —$CH{=}CH_2$ or —$CH_2CH_3$, and all other variables are as previously defined.

In another embodiment of the invention, $R^3$ is $C_1$-$C_8$ alkyl or $C_3$-$C_8$ cycloalkyl, and all other variables are as previously defined. In a preferred group of this embodiment, $R^3$ is —$C(CH_3)_3$, cyclohexyl or cyclopentyl, and all other variables are as previously defined.

In another embodiment of the invention, $R^5$ is H, and all other variables are as previously defined.

In another embodiment of the invention, Z is —O—, and all other variables are as previously defined.

In another embodiment of the invention, Y is —C(=O)—, and all other variables are as previously defined.

In another embodiment of the invention, W is H or —O—($C_1$-$C_6$) alkyl, and all other variables are as previously defined. In a preferred group of this embodiment, W is H or —$OCH_3$.

In another embodiment of the invention, A is —$C(R^{16})$— and all other variables are as previously defined. In a preferred group of this embodiment, $R^{16}$ is H.

In another embodiment of the invention, M is $C_1$-$C_{12}$ alkylene wherein said alkylene is optionally substituted with 1 or 2 substituents selected from the group consisting of $C_1$-$C_8$ alkyl, and all other variables are as previously defined. In a preferred group of this embodiment, M is selected from the group consisting of —$(CH_2)_5$—, —$(CH_2)_3CH(CH_3)CH_2$—, and —$(CH_2)_3C(CH_3)_2CH_2$—, and all other variables are as previously defined.

The present invention also includes pharmaceutical compositions containing a compound of the present invention and methods of preparing such pharmaceutical compositions. The present invention further includes methods of treating or preventing one or more symptoms of HCV infection.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts and/or hydrates thereof. These compounds and their pharmaceutically acceptable salts and/or hydrates are HCV protease inhibitors (e.g., HCV NS3 protease inhibitors). The present invention also includes compounds of formulae II, II-A, II-B, III, III-A and III-B wherein variables n, $R^1$, $R^2$, $R^3$, Y, Z, M, W, A, $R^5$ and $R^{11}$ are as defined for formula I.

II

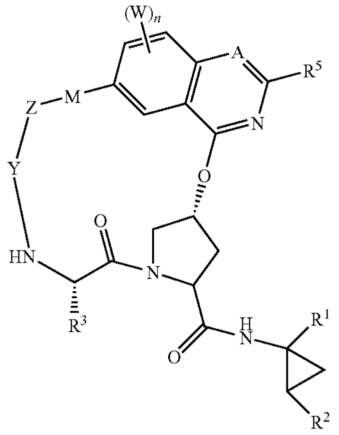

II-A

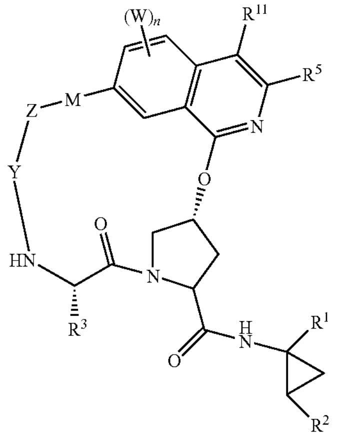

II-B

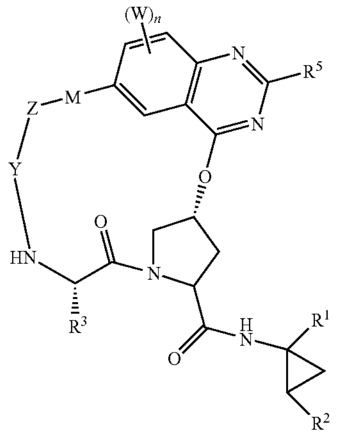

-continued

III

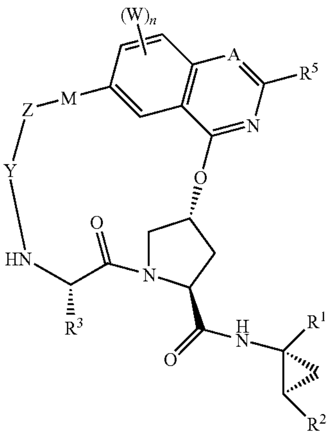

III-A

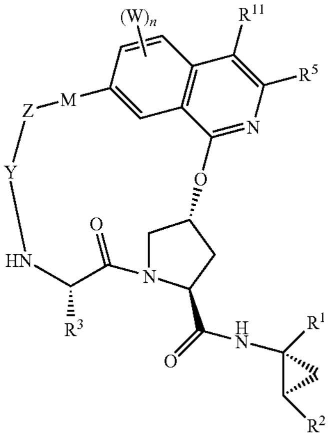

III-B

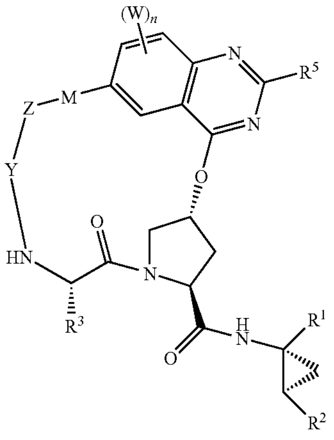

Other embodiments of the present invention include the following:

(a) A pharmaceutical composition comprising an effective amount of a compound of formula I, II, II-A, II-B, III, III-A, or III-B and a pharmaceutically acceptable carrier.

(b) The pharmaceutical composition of (a), further comprising a second therapeutic agent selected from the group consisting of a HCV antiviral agent, an immunomodulator, and an anti-infective agent.

(c) The pharmaceutical composition of (b), wherein the HCV antiviral agent is an antiviral selected from the group consisting of a HCV protease inhibitor and a HCV NS5B polymerase inhibitor.

(d) A pharmaceutical combination which is (i) a compound of formula I, II, II-A, II-B, III, III-A, or III-B and (ii) a second therapeutic agent selected from the group consisting of a HCV antiviral agent, an immunomodulator, and an anti-infective agent; wherein the compound of formula I, II, II-A, II-B, III, III-A, or III-B and the second therapeutic agent are each employed in an amount that renders the combination effective for inhibiting HCV NS3 protease, or for treating or preventing infection by HCV.

(e) The combination of (d), wherein the HCV antiviral agent is an antiviral selected from the group consisting of a HCV protease inhibitor and a HCV NS5B polymerase inhibitor.

(f) A method of inhibiting HCV NS3 protease in a subject in need thereof which comprises administering to the subject an effective amount of a compound of formula I, II, II-A, II-B, III, III-A, or III-B.

(g) A method of preventing or treating infection by HCV in a subject in need thereof which comprises administering to the subject an effective amount of a compound of formula I I, II, II-A, II-B, III, III-A, or III-B.

(h) The method of (g), wherein the compound of formula I, II, II-A, II-B, III, III-A, or III-B is administered in combination with an effective amount of at least one second therapeutic agent selected from the group consisting of a HCV antiviral agent, an immunomodulator, and an anti-infective agent.

(i) The method of (h), wherein the HCV antiviral agent is an antiviral selected from the group consisting of a HCV protease inhibitor and a HCV NS5B polymerase inhibitor.

(j) A method of inhibiting HCV NS3 protease in a subject in need thereof which comprises administering to the subject the pharmaceutical composition of (a), (b), or (c) or the combination of (d) or (e).

(k) A method of preventing or treating infection by HCV in a subject in need thereof which comprises administering to the subject the pharmaceutical composition of (a), (b), or (c) or the combination of (d) or (e).

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (k) above are understood to include all embodiments of the compounds, including such embodiments as result from combinations of embodiments.

The present invention also includes a compound of the present invention for use (i) in, (ii) as a medicament for, or (iii) in the preparation of a medicament for: (a) inhibiting HCV NS3 protease, or (b) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "haloalkyl" refers to an alkyl group wherein a hydrogen has been replaced by a halogen. The term "alkoxy" refers to an "alkyl-O—" group.

The term "alkylene" refers to any linear or branched chain alkylene group (or alternatively "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is $—(CH_2)_{1-6}—$, and sub-classes of particular interest include $—(CH_2)_{1-4}—$, $—(CH_2)_{1-3}—$, $—CH_2)_{1-2}—$, and $—CH_2—$. Also of interest is the alkylene $—CH(CH_3)—$.

The terms "cycloalkyl" refers to any cyclic ring of an alkane or alkene having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl. The term "cycloalkoxy" refers to a "cycloalkyl-O—" group.

The term "halogen" (or "halo") refers to fluorine, chlorine, bromine and iodine (alternatively referred to as fluoro, chloro, bromo, and iodo).

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

When any variable (e.g., $R^7$ and $R^{10}$) occurs more than one time in any constituent or in formula I, II, II-A, II-B, III, III-A, or III-B or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

Terms referring to 2 substituents "on adjacent carbon atoms," which "optionally taken together" form specified cyclic rings, and 2 substituents "on the same carbon atom," which "optionally taken together" form specified cyclic rings, mean that the 2 substituents can form a ring that includes both of the adjacent carbon atoms, or can form a ring that includes the same carbon atom. For example, ring 1 shown below is formed by two single carbon substituents each attached to adjacent carbon atoms, and ring 2 shown below is formed by two single carbon substituents each attached to the same carbon atom:

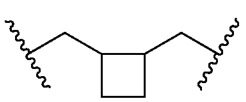

ring 1

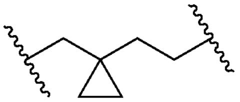

ring 2

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, certain of the compounds of the present invention can exist as tautomers. For the purposes of the present invention a reference to a compound of formula I, II, II-A, II-B, III, III-A, or III-B is a reference to the compound per se, or to any one of its tautomers per se, or to mixtures of two or more tautomers.

The compounds of the present inventions are useful in the inhibition of HCV protease (e.g., HCV NS3 protease) and the prevention or treatment of infection by HCV. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus the compounds of this invention are commercial products to be sold for these purposes.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound or salt (or hydrate) and other agents.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HCV NS3 protease and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HCV NS3 protease and preventing or treating HCV infection, the compounds of the present invention, optionally in the form of a salt or a hydrate, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences,* 18th edition, edited by A. R. Gennaro, Mack Publishing Co., 1990.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention also relates to a method of inhibiting HCV NS3 protease, inhibiting HCV replication, or preventing or treating HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include, but are not limited to, ribavirin, levovirin, viramidine, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as ROFERON interferon available from Hoffmann-LaRoche, Nutley, N.J.), pegylated interferon-α2a (PEGASYS), interferon-β2b (such as INTRON-A interferon available from Schering Corp., Kenilworth, N.J.), pegylated interferon-α2b (PEGINTRON), a recombinant consensus interferon (such as interferon alphacon-1), and a purified interferon-α product. Amgen's recombinant consensus interferon has the brand name Infergen®. Levovirin is the L-enantiomer of ribavirin which has shown immunomodulatory activity similar to ribavirin. Viramidine represents an analog of ribavirin disclosed in WO 01/60379 (assigned to ICN Pharmaceuticals). In accordance with the method of the present invention, the individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB-2337262, WO 02/48116, WO 02/48172, and U.S. Pat. No. 6,323,180.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in WO 97/41211 and WO 01/00622 (assigned to Vertex); another IMPDH inhibitor, such as that disclosed in WO 00/25780 (assigned to Bristol-Myers Squibb); or mycophenolate mofetil [see A. C. Allison and E. M. Eugui, *Agents Action,* 44 (Suppl.): 165 (1993)].

For the treatment of HCV infection, the compounds of the present invention may also be administered in combination with the antiviral agent amantadine (1-aminoadamantane) [for a comprehensive description of this agent, see J. Kirschbaum, *Anal. Profiles Drug Subs.* 12: 1-36 (1983)].

The compounds of the present invention may also be combined for the treatment of HCV infection with antiviral 2'-C-branched ribonucleosides disclosed in R. E. Harry-O'Kuru, et al., *J. Org. Chem.,* 62: 1754-1759 (1997); M. S. Wolfe, et al., *Tetrahedron Lett.,* 36: 7611-7614 (1995); U.S. Pat. No. 3,480,613 (Nov. 25, 1969); International Publication Number WO 01/90121 (29 Nov. 2001); International Publication Number WO 01/92282 (6 Dec. 2001); and International Publication Number WO 02/32920 (25 Apr. 2002); and International Publication Number WO 04/002999 (8 Jan. 2004); and International Publication Number WO 04/003000 (8 Jan. 2004); and International Publication Number WO 04/002422 (8 Jan. 2004); the contents of each of which are incorporated by reference in their entirety. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in WO 02/51425 (4 Jul. 2002), assigned to Mitsubishi Pharma Corp.; WO 01/79246, WO 02/32920, and WO 02/48165 (20 Jun. 2002), assigned to Pharmasset, Ltd.; WO 01/68663 (Sep. 20, 2001), assigned to ICN Pharmaceuticals; WO 99/43691 (Sep. 2, 1999); WO 02/18404 (Mar. 7, 2002), assigned to Hoffmann-LaRoche; U.S. 2002/0019363 (Feb. 14, 2002); WO 02/100415 (Dec. 19, 2002); WO 03/026589 (Apr. 3, 2003); WO 03/026675 (Apr. 3, 2003); WO 03/093290 (Nov. 13, 2003); US 2003/0236216 (Dec. 25, 2003); US 2004/0006007 (Jan. 8, 2004); WO 04/011478 (Feb. 5, 2004); WO 04/013300 (Feb. 12, 2004); US 2004/0063658 (Apr. 1, 2004); and WO 04/028481 (Apr. 8, 2004); the content of each of these references is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in WO 02/057287, U.S. Pat. No. 6,777,395, WO 02/057425, US 2004/0067901, WO 03/068244, WO 2004/000858, WO 04/003138 and WO 2004/007512; the content of each is incorporated herein by reference in its entirety. Other such HCV polymerase inhibitors include, but are not limited to, valopicitabine (NM-283; Idenix) and 2'-F-2'-beta-methylcytidine (see also WO 2005/003147, assigned to Pharmasset, Ltd.).

In one embodiment, nucleoside HCV NS5B polymerase inhibitors that are used in combination with the present HCV NS3 protease inhibitors are selected from the following compounds:

4-amino-7-(2-C-methyl-β-D-arabinofuranosyl)-7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-$C_{12}$-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4(3H)-one; 2-amino-5-methyl-7-(2-C, 2-O-dimethyl-β-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-β-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; or a pharmaceutically acceptable salt thereof.

The compounds of the present invention may also be combined for the treatment of HCV infection with non-nucleoside inhibitors of HCV polymerase such as those disclosed in WO 01/77091 (18 Oct. 2001), assigned to Tularik, Inc.; WO 01/47883 (5 Jul. 2001), assigned to Japan Tobacco, Inc.; WO 02/04425 (17 Jan. 2002), assigned to Boehringer Ingelheim; WO 02/06246 (24 Jan. 2002), assigned to Istituto di Ricerche di Biologia Moleculare P. Angeletti S. P. A.; WO 02/20497 (3 Mar. 2002); WO 2005/016927 (in particular JTK003), assigned to Japan Tobacco, Inc.; the content of each is incorporated herein by reference in its entirety; and HCV-796 (Viropharma Inc.).

The HCV NS3 protease inhibitory activity of the present compounds may be tested using assays known in the art. One such assay is HCV NS3 protease time-resolved fluorescence (TRF) assay as described below and in WO 2006/102087. Other examples of such assays are described in e.g., International patent publication WO 2005/046712. Compounds useful as HCV NS3 protease inhibitors would have a $K_i$ less than 50 μM, more preferably less than 10 μM, and even more preferably less than 100 nM.

The present invention also includes processes for making compounds of formula I, II, II-A, II-B, III, III-A, or The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice. The examples are not to be construed as limitations on the scope or spirit of the invention.

General Description of Synthesis

The compounds of the present invention may be synthesized as outlined in the general Schemes 1, 2 and 3.

Scheme 1

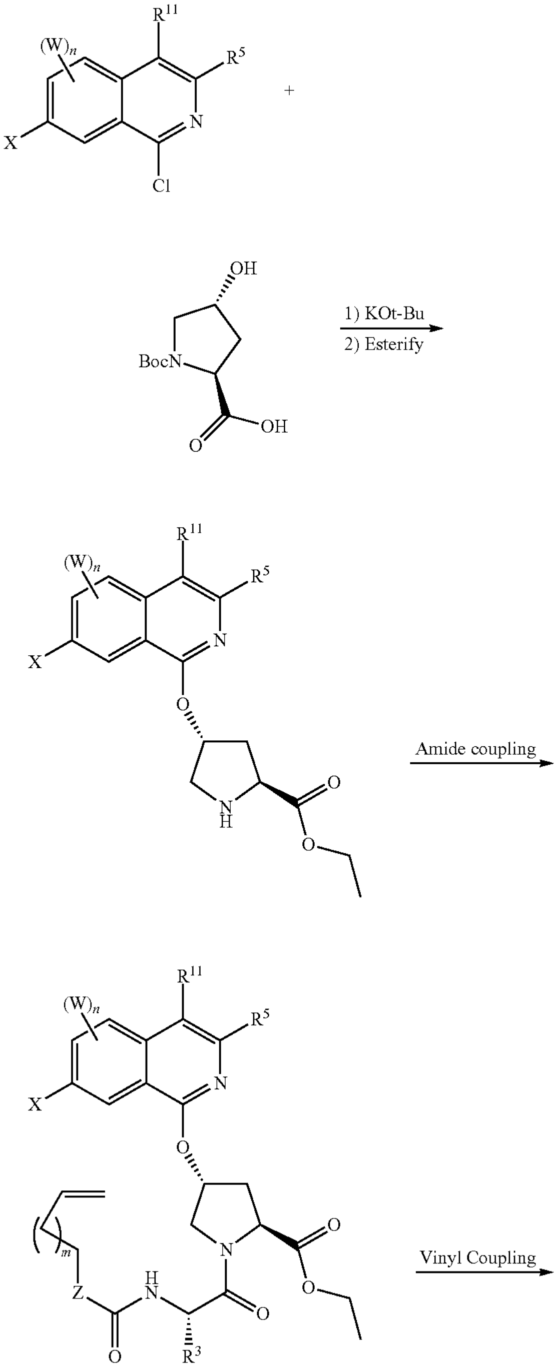

-continued

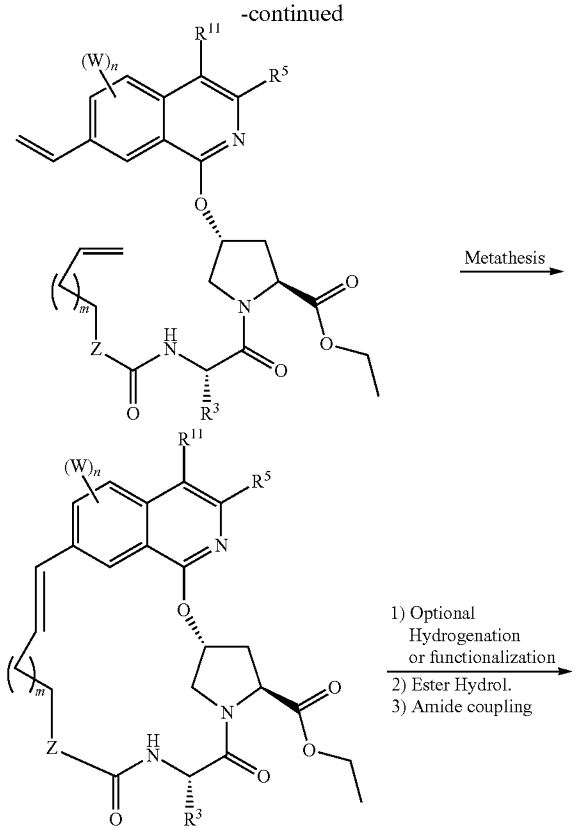

-continued

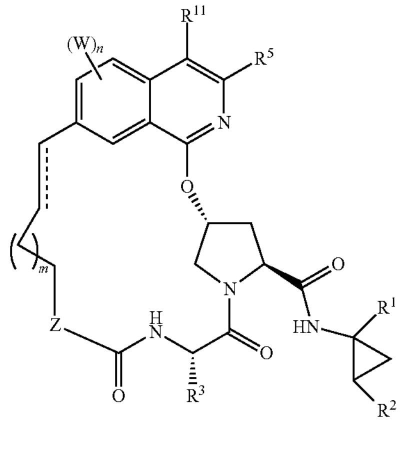

Scheme 1 (m=0-9) outlines the synthesis of a representative molecule. An appropriately protected 4-hydroxyproline derivative (for example, a carbamate protected nitrogen) can be reacted with potassium t-butoxide or equivalent reagent and then reacted with an appropriately substituted chloroisoquinoline. The acid can then be esterified with acid in an appropriate alcohol solvent. These conditions also remove the BOC protecting group on the proline nitrogen.

Scheme 2

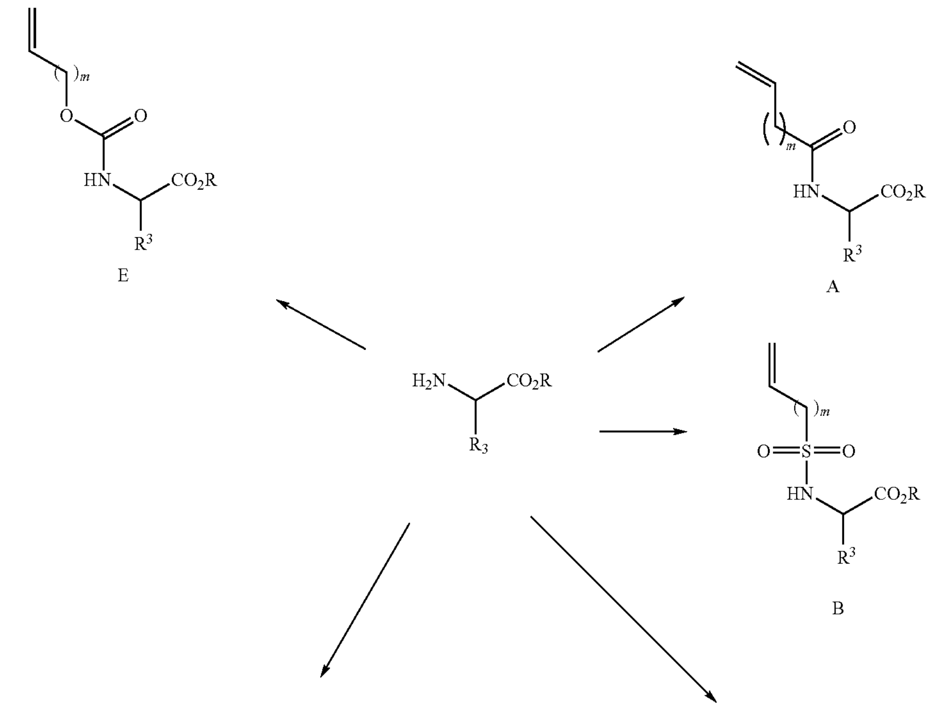

-continued

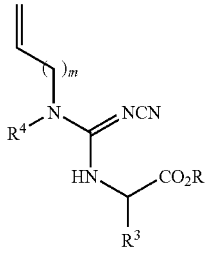

D

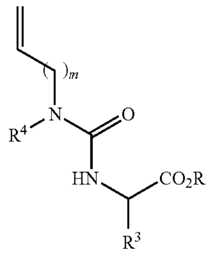

C

Scheme 2 describes the synthesis of the olefin-containing amino acid portion. An amino acid (either commercially available or may be prepared readily using known methods in the art) in which the acid functionality is protected as an ester (for example, R=methyl) can be converted to amides A by coupling an olefinic carboxylic acid utilizing a wide range of peptide coupling agents known to those skilled in the art such as DCC, EDC, BOP, TBTU, etc. Preparation of the Sulfonamides B can be Accomplished by Reaction with the Appropriate Sulfonyl chloride in an organic solvent (e.g., THF) with an amine base as scavenger. Urea derivatives C may be prepared by reacting the aminoester with a reagent such as carbonyldiimidazole, to form an intermediate isocyanate (Catalano et al., WO 03/062192) followed by addition of a second olefin-containing amine. Alternatively, phosgene, diphosgene or triphosgene may be used in place of carbonyldiimidazole. Cyanoguanidine derivatives D can be prepared by reaction of the amino acid ester with diphenyl C-cyanocarbonimidate in an organic solvent, followed by addition of a second olefin-containing amine. Carbamate derivatives E may be prepared by reacting an olefin-containing alcohol with carbonyldiimidazole (or phosgene, triphosgene or diphosgene) in an organic solvent, followed by addition of the amino ester.

Following functionalization of the amine, the ester can be hydrolyzed under a range of basic conditions known to those skilled in the art (Theodora W. Greene, *Protective Groups in Organic Synthesis*, Third Edition, John Wiley and Sons, 1999).

Deprotection of the carbamate protecting group on the proline portion may be carried out by a variety of methods known to persons skilled in the art (Theodora W. Greene, *Protective Groups in Organic Synthesis*, Third Edition, John Wiley and Sons, 1999).

To complete the synthesis of the compounds of this invention, the amino acid derivative can be coupled to the proline derivative via a wide range of peptide coupling reagents such as DCC, EDC, BOP, TBTU etc (see Scheme 1). The alkenyl functionality may be introduced at this stage by palladium-catalyzed reaction of a halide substituent such as bromide or iodide, or other functionality such as a triflate with an organometallic reagent such as a vinyl or allyltrialkyltin. Macrocyclization is then achieved by an olefin metathesis using a range of catalysts that have been described in the literature for this purpose. At this stage, the olefinic bond produced in the ring-closing metathesis may be optionally hydrogenated to give a saturated linkage or functionalized in alternative ways such as cyclopropanation. The proline ester is then hydrolyzed under basic conditions and coupled with an appropriate cyclopropyl containing P1 fragment, the syntheses of which have been described previously (Llinas-Brunet et al., U.S. Pat. No. 6,323,180; Chaudhary, WO 2006/020276) and subjected to an additional hydrolysis step to provide the final compounds.

Scheme 3

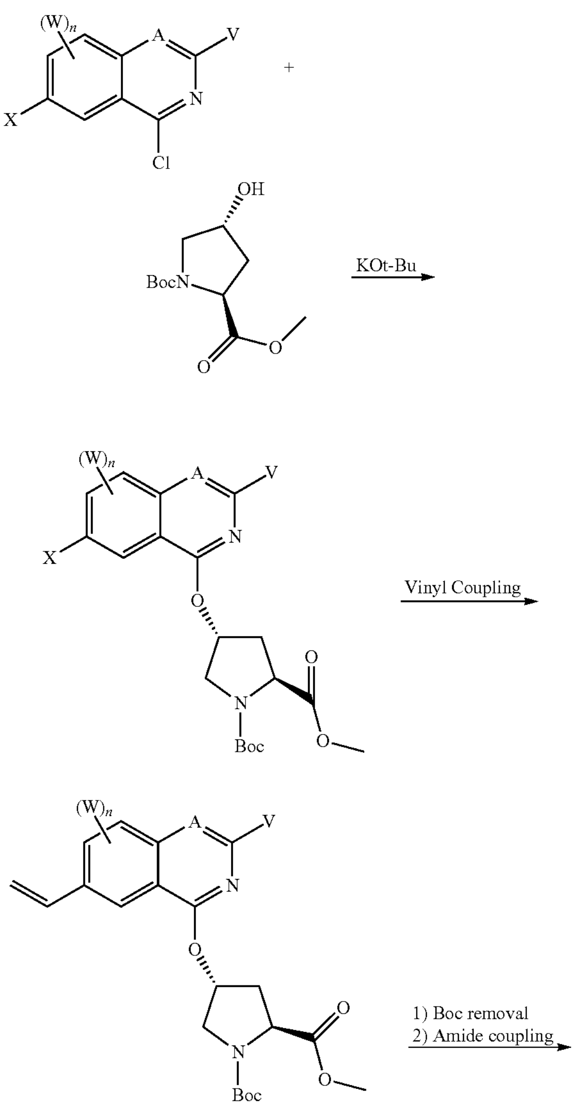

-continued

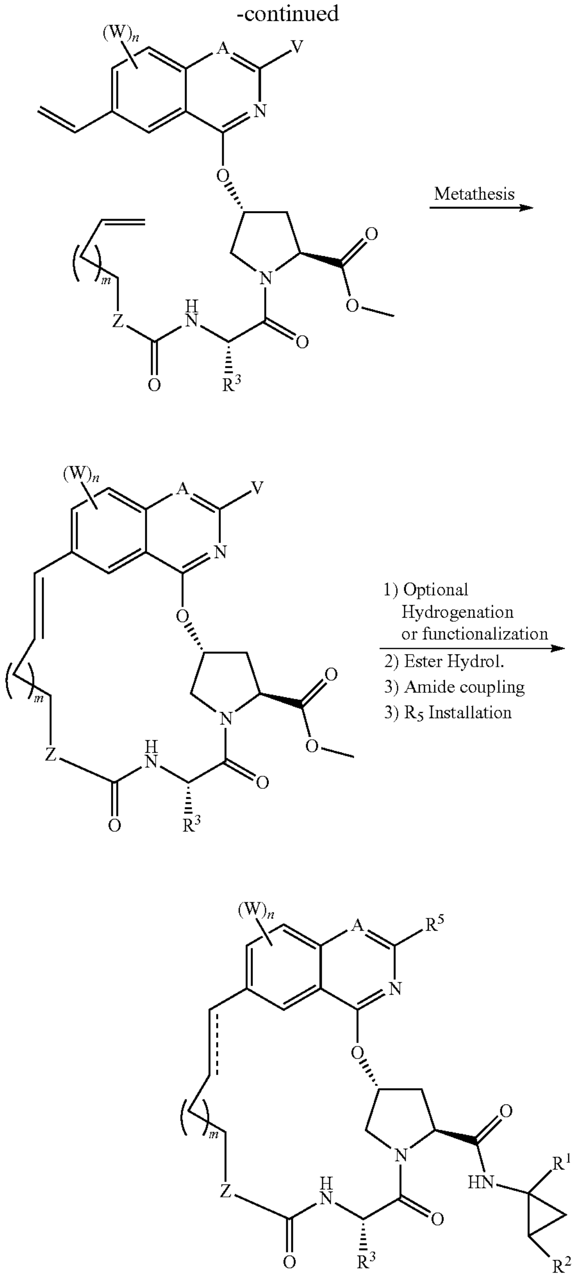

F

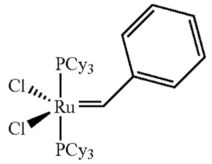

G

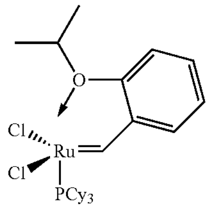

H

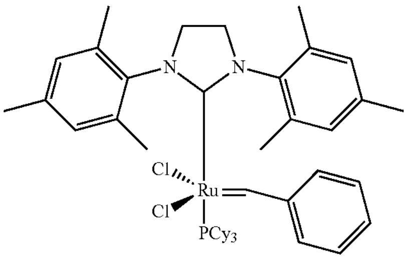

J

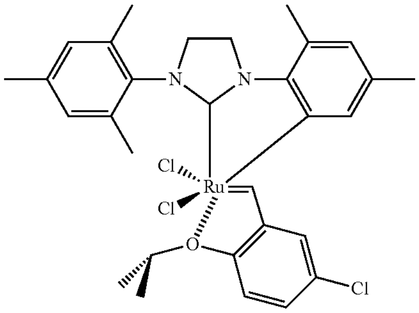

K

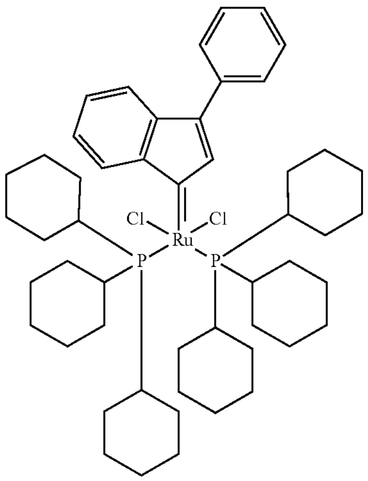

Molecules with 3-substituted isoquinolines or 2-substituted quinazolines may be prepared according to Scheme 3 (wherein V is, for example, halo such as chloro). An appropriately substituted 3-halo isoquinoline or 2-halo quinazoline can be employed in a sequence similar to the route shown in Scheme 1. In a final additional step, an $R^5$ group can be installed via displacement reactions or metal-mediated coupling reactions.

Olefin metathesis catalysts include the following Ruthenium-based species: F: Miller et al *J. Am. Chem. Soc* 1996, 118, 9606; G: Kingsbury et al *J. Am. Chem. Soc* 1999, 121, 791; H: Scholl et al Org. Lett. 1999, 1, 953; Hoveyda et al US2002/0107138; K: Furstner et al. J. Org. Chem. 1999, 64, 8275. The utility of these catalysts in ring-closing metathesis is well known in the literature (e.g. Trnka and Grubbs, *Acc. Chem. Res.* 2001, 34, 18).

-continued

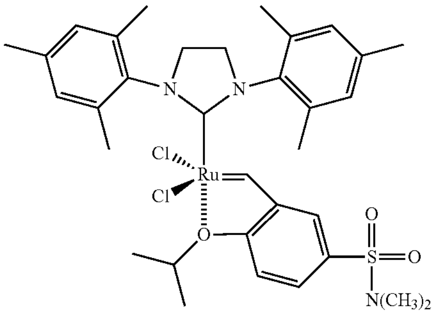

Zhan ruthenium metathesis catalyst RC-303
(Zhan catalyst 1B, RC-303, Zannan Pharma Ltd.)

LIST OF ABBREVIATIONS

BOP Benzotriazole-1-yl-oxy-tris-(dimethylamino)-phosphonium hexafluorophosphate Brosyl chloride 4-Bromophenyl sulfonylchloride
$CH_3CN$ Acetonitrile
DABCO 1,4-Diazabicyclo[2.2.2]octane
DBU 1,8-Diazabicyclo[5.4.0]undec-7-ene
DCC Dicyclohexylcarbodiimide
DCE Dichloroethane
DCM Dichloromethane
DMAP 4-Dimethylamino pyridine
DIPEA Diisoproylethylamine
DMF Dimethylformamide
DMSO Dimethyl Sulfoxide
EDC N-(3-Dimethylaminopropyl)-N'-ethylcarbodiimide
$Et_3N$ Triethylamine
$Et_2O$ Diethyl ether
EtOAc Ethyl Acetate
EtOH Ethanol
HATU 0-(7-Azabenzotriazol-1-yl)-N,N,N',N'-tetramethyluronium hexafluorophosphate
HBr Hydrobromic acid
HCl Hydrochloric acid
HOAc Acetic acid
HOAt 1-Hydroxy-7-azabenzotriazole
LiOH Lithium hydroxide
MeOH Methanol
$MgSO_4$ Magnesium Sulfate
$Na_2SO_4$ Sodium sulfate
$NaHCO_3$ Sodium bicarbonate
NaOH Sodium hydroxide
$NH_4Cl$ Ammonium chloride
$NH_4OH$ Ammonium hydroxide
Nle Norleucine
Pd/C Palladium on carbon
PhMe Toluene
$PPh_3$ Triphenylphosphine
RT Room temperature
TBAF Tetrabutylammonium fluoride
TBTU O-Benzotriazol-1-yl-N,N,N',N'-tetramethyluronium tetrafluoroborate
THF Tetrahydrofuran Synthesis of Intermediates:

| Intermediate # | Structure | Name | Lit. Reference |
|---|---|---|---|
| A1 | 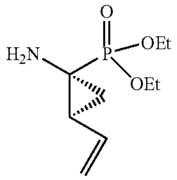 | diethyl [(1S,2R)-1-amino-2-vinylcyclopropyl]phosphonate | Chaudhary WO 2006/020276 |
| A2 | 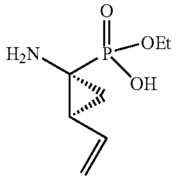 | ethyl hydrogen [(1S,2R)-1-amino-2-vinylcyclopropyl]phosphonate | Chaudhary WO 2006/020276 |
| A3 | 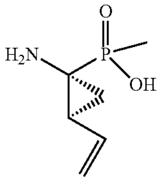 | [(1S,2R)-1-amino-2-vinylcyclopropyl]methylphosphinic acid | Chaudhary WO 2006/020276 |
| A4 | 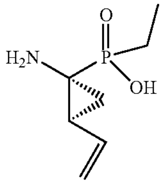 | [(1S,2R)-1-amino-2-vinylcyclopropyl]ethylphosphinic acid | Chaudhary WO 2006/020276 |

-continued

| Intermediate # | Structure | Name | Lit. Reference |
|---|---|---|---|
| A5 | 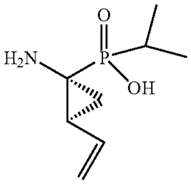 | [(1S,2R)-1-amino-2-vinylcyclopropyl]isopropylphosphinic acid | Chaudhary WO 2006/020276 |
| A6 | 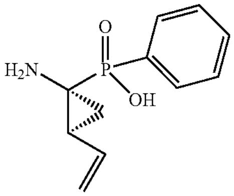 | [(1S,2R)-1-amino-2-vinylcyclopropyl]phenylphosphinic acid | Chaudhary WO 2006/020276 |
| A7 | 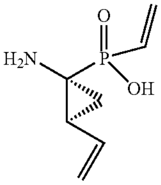 | [(1S,2R)-1-amino-2-vinylcyclopropyl]vinylphosphinic acid | Chaudhary WO 2006/020276 |
| A8 | 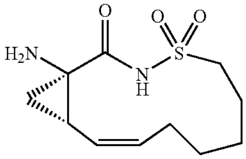 | 1-amino-4-thia-3-azabicyclo[10.1.0] tridec-10-en-2-one 4,4-dioxide | Chaudhary WO 2006/020276 |
| A9 | 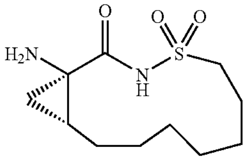 | 1-amino-4-thia-3-azabicyclo[10.1.0]tridecan-2-one 4,4-dioxide | Chaudhary WO 2006/020276 |

By hydrogenation of the intermediates above, or a suitable intermediate in their preparation, for example by treatment in an appropriate solvent or solvent mixture with a palladium, platinum or rhodium catalyst, the following intermediates can be prepared by a person skilled in the art.

| Intermediate # | Structure | Name |
|---|---|---|
| A10 | 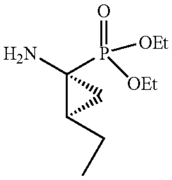 | diethyl [(1S,2S)-1-amino-2-ethylcyclopropyl]phosphonate |

-continued

| Intermediate # | Structure | Name |
|---|---|---|
| A11 | 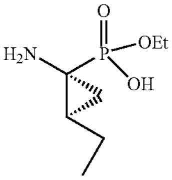 | ethyl hydrogen [(1S,2S)-1-amino-2-ethylcyclopropyl]phosphonate |
| A12 | 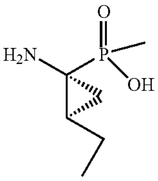 | [(1S,2S)-1-amino-2-ethylcyclopropyl]methylphosphinic acid |

-continued

| Intermediate # | Structure | Name |
|---|---|---|
| A13 | 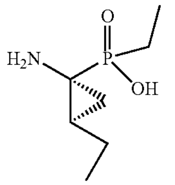 | [(1S,2S)-1-amino-2-ethylcyclopropyl]ethyl-phosphinic acid |
| A14 | 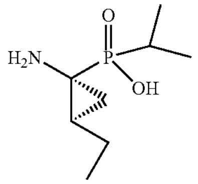 | [(1S,2S)-1-amino-2-ethylcyclopropyl]iso-propylphosphinic acid |
| A15 | 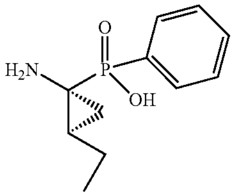 | [(1S,2S)-1-amino-2-ethylcyclopropyl]phenyl-phosphinic acid |

Intermediates B

Intermediate B1: N-[(pent-4-en-1-yloxy)carbonyl]-L-norleucine

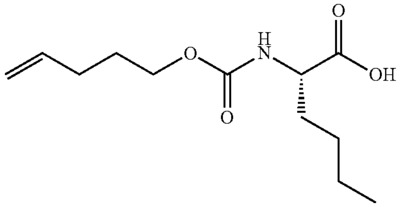

To a solution of 1-penten-4-ol (0.95 g, 11.0 mmol) in DMF (15 mL) at 0° C. was added carbonyldiimidazole (1.79 g, 11.0 mmol). The reaction mixture was warmed to RT and stirred for 30 minutes. L-norleucine methyl ester hydrochloride (2.0 g, 11.0 mmol) was then added, the reaction mixture was heated to 50° C. and stirred for 15 minutes. Upon cooling, the reaction mixture was diluted with ethyl ether and washed twice with water. The organic layer was dried over $Na_2SO_4$, filtered and concentrated. The crude product was purified by silica gel chromatography (gradient elution 10 to 90% EtOAc in hexanes) to afford 2.1 g (74%) methyl N-[(pent-4-en-1-yloxy)carbonyl]-L-norleucinate as a clear oil.

To a stirred solution of methyl N-[(pent-4-enyloxy)carbonyl]-L-norleucinate (8.50 g, 33.03 mmol) in THF (20 mL) was added 1N NaOH (20 mL). This reaction solution was stirred at RT for 3 hours, then acidified to pH 3 with 1N HCl and extracted with (3×250 mL) EtOAc. The combined EtOAc layer was washed with 50 mL water, 50 mL brine, dried over $Na_2SO_4$, filtered and concentrated to give 7.09 g (88%) of the title product as clear oil. LRMS (ESI) m/z 244 $[(M+H)^+$, calcd for $C_{12}H_{22}NO_4$: 244].

Intermediate B2: (2S)-3,3-dimethyl-2-{[(pent-4-en-1-yloxy)carbonyl]amino}butanoic acid

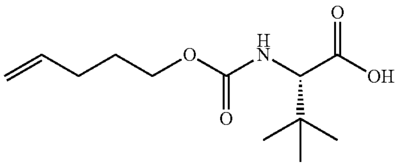

DIPEA (9.85 g, 76.2 mmol) was added dropwise to a 0° C. solution of 4-penten-1-ol (7.22 g, 83.9 mmol) and triphosgene (11.3 g, 38.1 mmol) in 160 mL dioxane. The resulting white suspension was stirred for 5 minutes at 0° C., then allowed to warm to 25° C. over 1 hour. The suspension was cooled to 0° C. with an ice bath and 1 N NaOH (76.2 mL) and L-t-butylglycine (10.0 g, 76.2 mmol) were added. The reaction mixture was warmed to 25° C. and stirred for 18 hours. The dioxane was removed in vacuo and the reaction mixture was basified to pH 12 with 1 N NaOH. The aqueous layer was extracted with DCM (3×150 mL), then acidified to pH~1 with 6 N HCl. The aqueous layer was extracted with DCM (3×150 mL). The combined organic layers were dried over $MgSO_4$ and concentrated to give the compound as a tan oil (13.7 g, 73.9% yield). LRMS (ESI) m/z 244 $[(M+H)^+$; calcd for $C_{12}H_{22}NO_4$ 244].

The following carbamate intermediates (B3-B49) were prepared using the chemistry described for the preparation Intermediate B2, by utilizing the appropriate amino acid and alcohol or the preparation of Intermediate B1 by utilizing the appropriate alcohol and amino ester.

| Int. | Amino Acid | Alcohol | Structure | Name | LRMS $(M + H)^+$ |
|---|---|---|---|---|---|
| B1 | L-Norleucine | 4-Penten-1-ol | 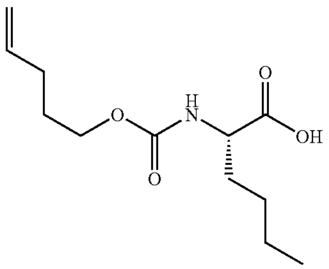 | N-[(Pent-4-en-1-yloxy)carbonyl]-L-norleucine (Intermediate 1) | 244.3 |

-continued

| Int. | Amino Acid | Alcohol | Structure | Name | LRMS (M + H)+ |
|---|---|---|---|---|---|
| B2 | L-t-Butyl-glycine | 4-Penten-1-ol | 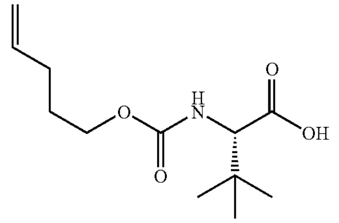 | (2S)-3,3-Dimethyl-2-{[(pent-4-en-1-yloxy)carbonyl]amino}butanoic acid | 244.2 |
| B3 | L-Valine | 4-Penten-1-ol | 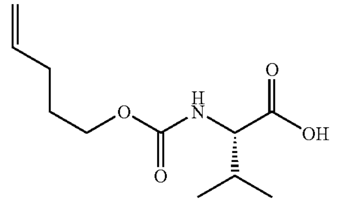 | N-[(Pent-4-en-1-yloxy)carbonyl]-L-valine | 230.3 |
| B4 | L-t-Butyl-glycine | 2,2-Dimethyl-4-penten-1-ol Ref: *J. Org. Chem* (1981), 46, 1177-1182. | 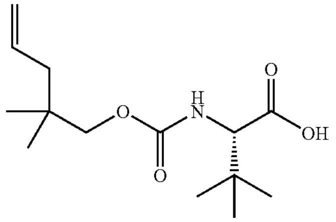 | N-{[(2,2-Dimethylpent-4-en-1-yl)oxy]carbonyl}-3-methyl-L-valine | 272.3 |
| B5 | L-t-Butyl-glycine | 5-Hexen-1-ol | 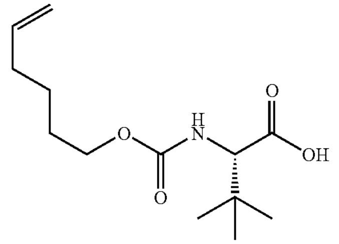 | N-[(Hex-5-en-1-yloxy)carbonyl]-3-methyl-L-valine | 258.3 |
| B6 | L-Phenyl-glycine | 4-Penten-1-ol | 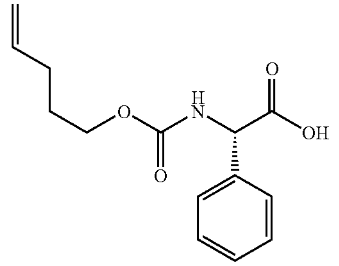 | (2S)-{[(Pent-4-en-1-yloxy)carbonyl]amino}(phenyl)acetic acid | 264.3 |
| B7 | L-t-Butyl-glycine | 6-Hepten-1-ol | 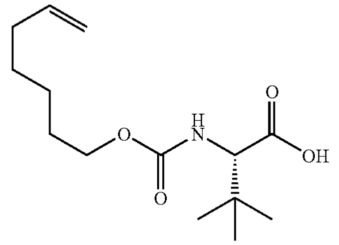 | N-[(Hept-6-en-1-yloxy)carbonyl]-3-methyl-L-valine | 272.3 |

-continued

| Int. | Amino Acid | Alcohol | Structure | Name | LRMS $(M + H)^+$ |
|---|---|---|---|---|---|
| B8 | L-Cyclohexyl-glycine | 4-Penten-1-ol | 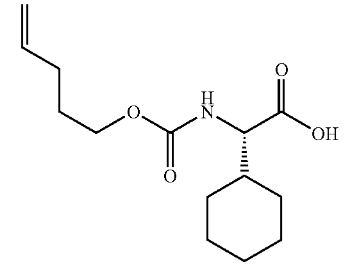 | (2S)-Cyclohexyl{[(pent-4-en-1-yloxy) carbonyl]amino} acetic acid | 270.3 |
| B9 | L-Phenyl alanine | 4-Penten-1-ol | 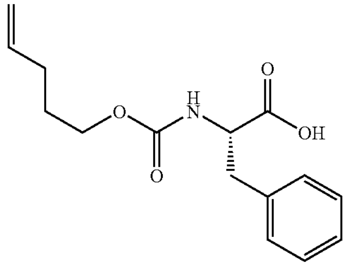 | N-[(Pent-4-en-1-yloxy)carbonyl] -L-phenylalanine | 278.2 |
| B10 | 3,3,3-Trifluoroalanine | 4-Penten-1-ol | 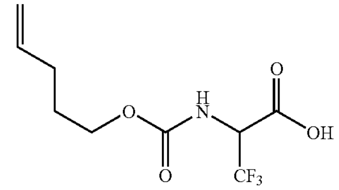 | 3,3,3-trifluoro-N-[(pent-4-en-1-yloxy)carbonyl] alanine | 256.2 |
| B11 | L-t-Butyl-glycine | 4-Pentyn-1-ol | 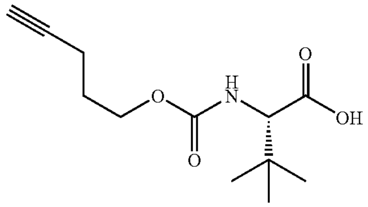 | 3-Methyl-N-[(pent-4-yn-1-yloxy) carbonyl] -L-valine | 242.2 |
| B12 | L-Norvaline | 4-Penten-1-ol | 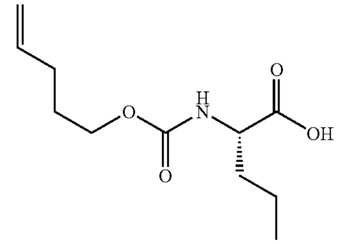 | N-[(Pent-4-en-1-yloxy)carbonyl]-L-norvaline | 230.3 |
| B13 | L-Cyclopentyl-glycine | 4-Penten-1-ol | 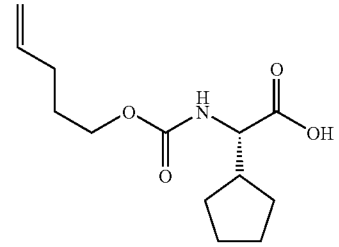 | (2,S)-Cyclopentyl {[(pent-4-en-1-yloxy)carbonyl] amino}acetic acid | 256.3 |

-continued

| Int. | Amino Acid | Alcohol | Structure | Name | LRMS (M + H)+ |
|---|---|---|---|---|---|
| B14 | 2-Amino-4,4,4-trifluorobutanoic acid | 5-Hexen-1-ol | 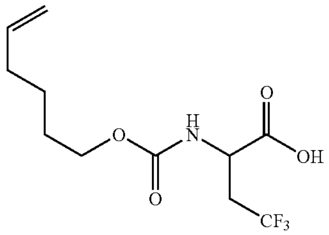 | 4,4,4-Trifluoro-2-{[(hex-5-en-1-yloxy)carbonyl] amino]butanoic acid | 305.2 (M + Na)+ |
| B15 | L-Leucine | 4-Penten-1-ol | 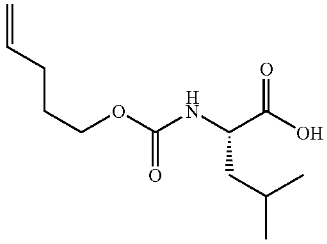 | N-[(Pent-4-en-1-yloxy)carbonyl]-L-leucine | 244.3 |
| B16 | L-Tryptophan | 4-Penten-1-ol | 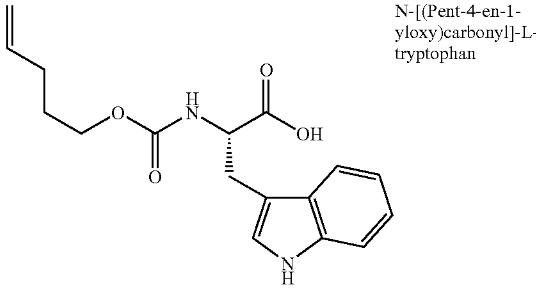 | N-[(Pent-4-en-1-yloxy)carbonyl]-L-tryptophan | 317.4 |
| B17 | O-(t-Butyl)-L-serine | 4-Penten-1-ol | 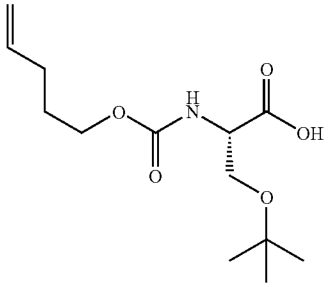 | O-(t-Butyl)-N-[(pent-4-en-1-yloxy)carbonyl] -L-serine | 218.3 (M-tBu)+ |
| B18 | 6,6,6-trifluoronorleu-cine | 5-Hexen-1-ol | 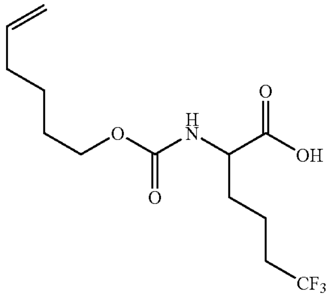 | 6,6,6-Trifluoro-N-[(hex-5-en-1-yloxy)carbonyl] norleucine | 353.2 (M + MeCN)+ |

-continued

| Int. | Amino Acid | Alcohol | Structure | Name | LRMS $(M + H)^+$ |
|---|---|---|---|---|---|
| B19 | Amino(2,3-dihydro-1H-inden-2-yl)acetic acid | 4-Penten-1-ol | 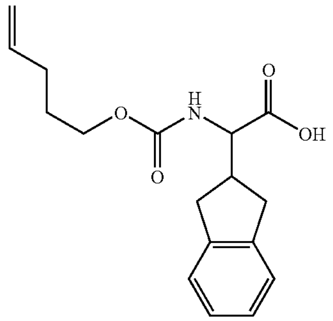 | 2,3-Dihydro-lH-inden-2-yl{[(pent-4-en-1-yloxy)arbonyl] amino}acetic acid | 304.3 |
| B20 | L-t-Butyl-glycine | (trans)-2-allylcyclohexanol Ref: *Tetrahedron* (2004), 60, 4837. | 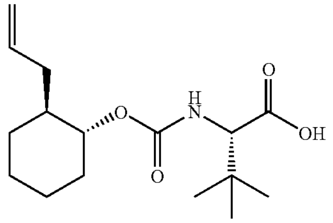 | N{[(trans)-2-Allylcyclohexyl] oxy}carbonyl)-3-methyl-L-valine | 298.4 |
| B21 | L-Cyclohexyl-glycine | 3-Buten-1-ol | 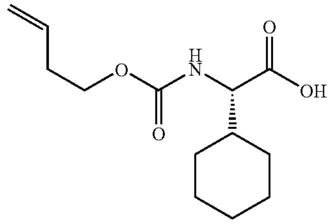 | (2S)-{[(But-3-en-1-yloxy)carbonyl] amino}(cyclohexyl) acetic acid | 256.2 |
| B22 | L-t-Butyl-glycine | 3-Buten-1-ol | 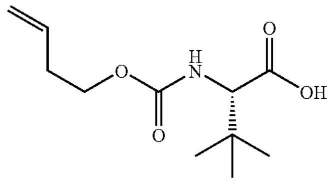 | N-[(But-3-en-1-yloxy)carbonyl]-3-methyl-L-valine | 230.3 |
| B23 | L-Cyclohexyl-glycine | 2,2-Dimethyl-4-penten-1-ol Ref: *J. Org. Chem* (1981), 46, 1177-1182. | 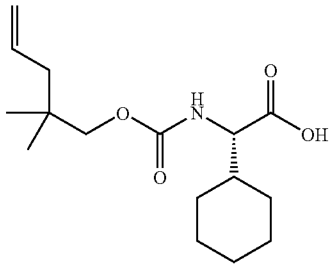 | (2S)-Cyclohexyl({[(2,2-dimethylpent-4-en-1-yl)oxy]carbonyl} amino)acetic acid | 298.3 |
| B24 | L-Cyclopentyl-glycine | 2,2-Dimethyl-4-penten-1-ol Ref: *J. Org. Chem* (1981), 46, 1177-1182. | 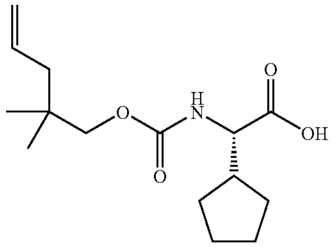 | (2S)-Cyclopentyl({[(2,2-dimethylpent-4-en-1-yl)oxy]carbonyl} amino)acetic acid | 284.3 |

-continued

| Int. | Amino Acid | Alcohol | Structure | Name | LRMS $(M + H)^+$ |
|---|---|---|---|---|---|
| B25 | L-t-Butyl-glycine | 2,2-Dimethylhex-5-en-1-ol Ref: *J. Org. Chem.* (1991), 56, 1623. | 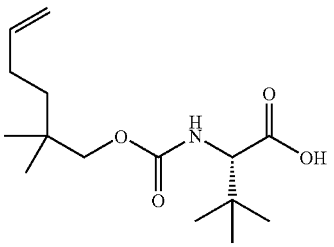 | N-{[(2,2-Dimethylhex-5-en-1-yl)oxy]carbonyl}-3-methyl-L-valine | 286.3 |
| B26 | L-Cyclohexyl-glycine | 6-Hepten-1-ol | 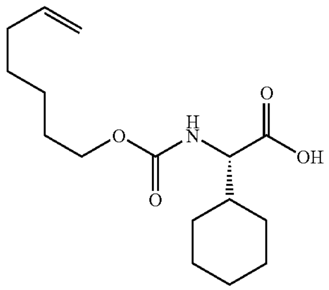 | (2S)-Cyclohexyl{[(hept-6-en-1-yloxy)carbonyl] amino}acetic acid | 298.3 |
| B27 | L-t-Butyl-glycine | 7-Octen-1-ol | 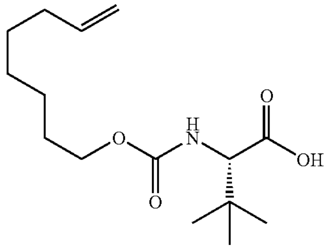 | 3-Methyl-N-[(oct-7-en-1-yloxy) carbonyl]-L-valine | 286.3 |
| B28 | L-Cyclohexyl-glycine | 5-Hexen-1-ol | 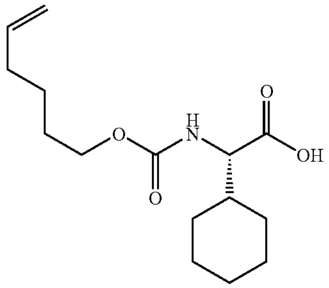 | (2S)-Cyclohexyl{[(hex-5-en-1-yloxy)carbonyl] amino}acetic acid | 284.4 |
| B29 | L-t-Butyl-glycine | (trans)-2-Allyl cyclopentanol Ref: *J. Chem. Soc, Perkin Trans 1* (1994), 11, 1377. | 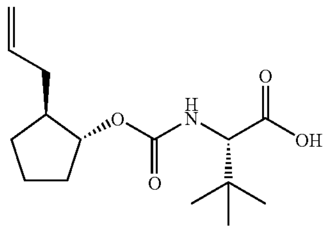 | N-({[(trans)-2-Allylcyclopentyl]oxy} carbonyl)-3-methyl-L-valine | 284.2 |

-continued

| Int. | Amino Acid | Alcohol | Structure | Name | LRMS (M + H)+ |
|---|---|---|---|---|---|
| B30 | L-Cyclohexyl-glycine | 1-Methylpent-4-en-1-ol Ref: *Tetrahedron Assym.* (1998), 9, 657. | 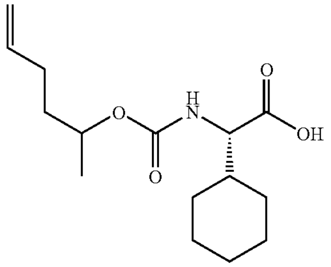 | (2S)-Cyclohexyl({[(1-methylpent-4-en-1-yl)oxy]carbonyl}amino)acetic acid | 284.2 |
| B31 | L-Cyclopentyl-glycine | 5-Hexen-1-ol | 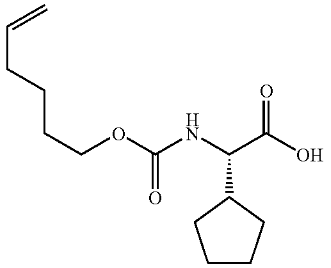 | (2S)-Cyclopentyl{[(hex-5-en-1-yloxy)carbonyl]amino}acetic acid | 270.3 |
| B32 | L-Cyclopentyl-glycine | 6-Hepten-1-ol | 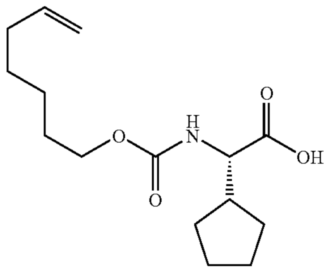 | (2S)-Cyclopentyl{[(hept-6-en-1-yloxy)carbonyl]amino)acetic acid | 284.4 |
| B33 | L-Cyclobutyl-glycine | 4-Penten-1-ol | 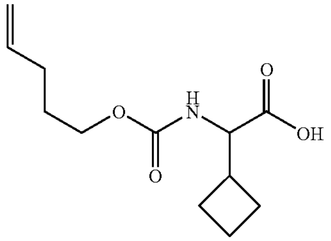 | Cyclobutyl{[(pent-4-en-1-yloxy)carbonyl]amino}acetic acid | 242.3 |
| B34 | L-Cyclopentyl-glycine | 2,2-Dimethylhex-5-en-1-ol Ref: *J. Org. Chem.* (1991), 56, 1623. | 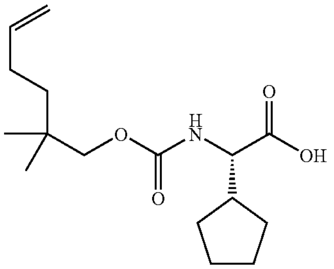 | (2S)-Cyclopentyl({[(2,2-dimethylhex-5-en-1-yl)oxy]carbonyl}amino)acetic acid | 298.3 |

-continued

| Int. | Amino Acid | Alcohol | Structure | Name | LRMS $(M + H)^+$ |
|---|---|---|---|---|---|
| B35 | L-Cyclohexyl-glycine | 2,2-Dimethylhex-5-en-1-ol Ref: *J. Org. Chem.* (1991), 56, 1623. | 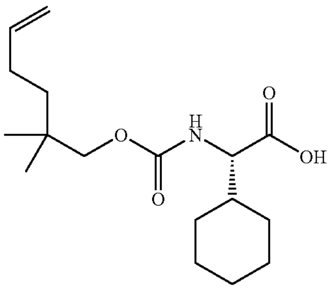 | (2S)-Cyclohexyl({[(2,2-dimethylhex-5-en-1-yl)oxy]carbonyl} amino)acetic acid | 312.3 |
| B36 | L-Cyclopentyl-glycine | 2,2-Dimethylhept-6-en-1-ol Ref: *J. Org. Chem.* (1980), 45, 2685. | 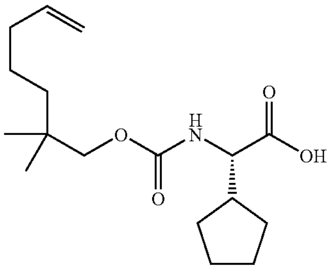 | (2S)-Cyclopentyl({[(2,2-dimethylhept-6-en-1-yl)oxy]carbonyl} amino)acetic acid | 312.2 |
| B37 | L-Cyclohexyl-glycine | 8-Nonen-1-ol | 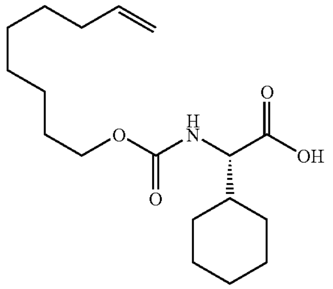 | (2S)-Cyclohexyl{[(non-8-en-1-yloxy)carbonyl] amino}acetic acid | 326.3 |
| B38 | L-Cyclopentyl-glycine | (trans)-2-Allyl cyclopentanol Ref: *J. Chem. Soc., Perkin Trans 1* (1994), 11, 1377. | 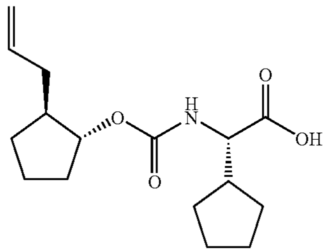 | (2S)-[({[(trans)-2-Allylcyclopentyl]oxy} carbonyl)amino] (cyclopentyl)acetic acid | 296.4 |
| B39 | L-Cyclohexyl-glycine | 2-Methylpent-4-en-1-ol Ref: *Tetrahedron* (1993), 49, 947. | 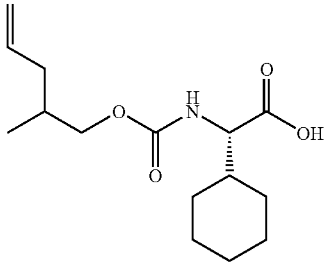 | (2S)-Cyclohexyl({[(2-methylpent-4-en-1-yl)oxy]carbonyl} amino)acetic acid | 284.4 |

-continued

| Int. | Amino Acid | Alcohol | Structure | Name | LRMS (M + H)$^+$ |
|---|---|---|---|---|---|
| B40 | L-Cyclohexyl-glycine | 2,2-Dimethylhept-6-en-1-ol Ref: *J. Org. Chem.* (1980), 45, 2685. | 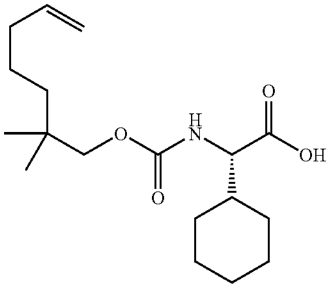 | (2S)-Cyclohexyl({[(2,2-dimethylhept-6-en-1-yl)oxy]carbonyl}amino)acetic acid | 326.4 |
| B41 | L-Cyclohexyl-glycine | (trans)-2-Allyl cyclopentanol Ref: *J. Chem. Soc, Perkin Trans 1* (1994), 11, 1377. | 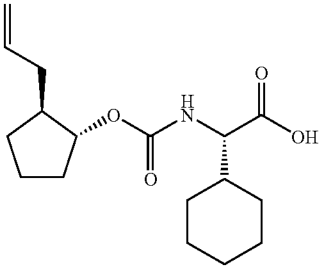 | (2S)-[({[(trans)-2-Allylcyclopentyl]oxy}carbonyl)amino](cyclohexyl) acetic acid | 310.5 |
| B42 | L-Cyclohexyl-glycine | (1-Allyl cyclopentyl) methanol Ref: *J. Org. Chem.* (1992), 57, 1727. | 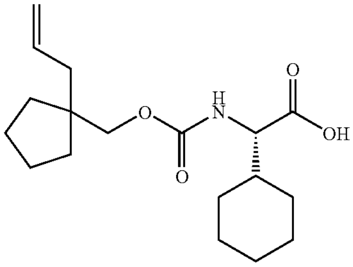 | (2S)-({[(1-Allylcyclopentyl) methoxy] carbonyl}amino) (cyclohexyl)acetic acid | 624.3 |
| B43 | L-Cyclohexyl-glycine | 2-Ethylpent-4-en-1-ol Ref: *Tetrahedron Lett.* (1985), 26, 6085. | 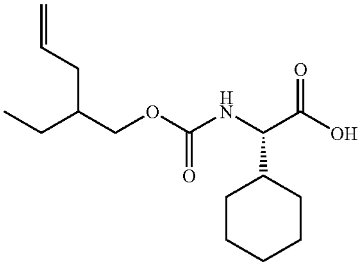 | (2S)-Cyclohexyl({[(2-ethylpent-4-en-1-yl)oxy]carbonyl}amino) acetic acid | 298.2 |
| B44 | L-Cyclopentyl-glycine | (1-Allyl cyclopropyl) methanol Ref: *Helv. Chim. Acta* (1986), 69, 1655. | 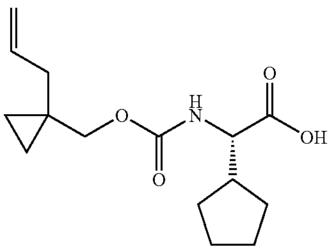 | (2S)-({[(1-Allylcyclopropyl) methoxy]carbonyl}amino)(cyclopentyl) acetic acid | 282.3 |

-continued

| Int. | Amino Acid | Alcohol | Structure | Name | LRMS (M + H)+ |
|---|---|---|---|---|---|
| B45 | L-Cyclohexyl-glycine | (1-Allyl cyclopropyl) methanol Ref: *Helv. Chim. Acta* (1986), 69, 1655. | 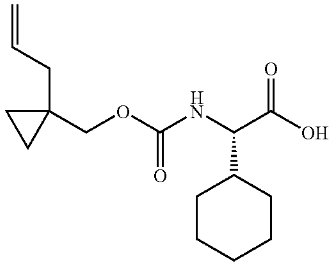 | (2S)-({[(1-Allylcyclopropyl) methoxy]carbonyl} amino)(cyclohexyl) acetic acid | 296.3 |
| B46 | L-t-Butyl-glycine | 2-Methylpent-4-en-1-ol Ref: *Tetrahedron* (1993), 49, 947. | 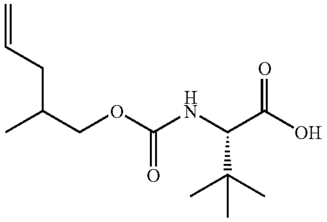 | 3-Methyl-N-{[(2-methylpent-4-en-1-yl)oxy]carbonyl}-L-valine | 258.3 |
| B47 | L-Cyclopentyl-glycine | (1-Allyl cyclopentyl) methanol Ref: *J. Org. Chem.* (1992), 57, 1727. | 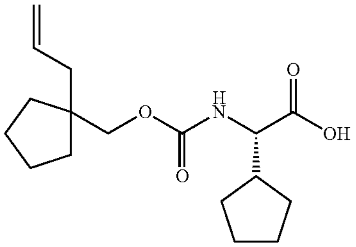 | (2S)-({[(1-Allylcyclopentyl) methoxy] carbonyl}amino) (cyclopentyl)acetic acid | 310.3 |
| B48 | L-Cyclopentyl-glycine | 2-Methylpent-4-en-1-ol Ref: *Tetrahedron* (1993), 49, 947. | 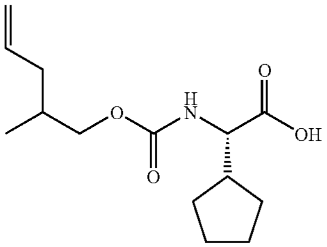 | (2S)-Cyclopentyl({[(2-methylpent-4-en-1-yl)oxy]carbonyl} amino)acetic acid | 270.2 |
| B49 | L-t-Butyl-glycine | Allyl alcohol | 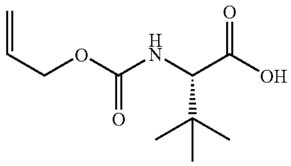 | N-[(allyloxy)carbonyl]-3-methyl-L-valine | 215.2 |

Intermediate B50: N-{[(1,1-Dimethylpent-4-en-1-yl) amino]carbonyl}-L-valine

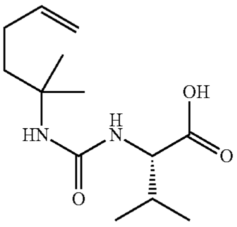

Step 1: Methyl N-(oxomethylene)-L-valinate

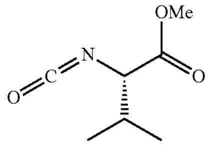

A mixture of L-valine methyl ester hydrochloride (10.0 g, 59.9 mmol), DCM (300 mL), and pyridine (19.3 mL, 240 mmol) was cooled in an ice/salt bath and a solution of 20% phosgene in PhMe (35.6 mL, 719 mmol) added dropwise, maintaining the reaction temperature below 5° C. during the addition. A white suspension resulted and after 1.5 hours, the reaction mixture was poured into ice-cold 1M HCl and extracted with DCM (2×500 mL). The combined organic phases were washed with brine, dried over anhydrous $MgSO_4$, and evaporated. Flash column chromatography on silica (95 hexanes/5 EtOAc) gave the title compound as a colorless oil (6.43 g). $^1$H NMR ($CDCl_3$ 500 MHz) δ 3.94 (d, J=4.0 Hz, 1H), 3.82 (s, 3H), 2.24 (m, 1H), 1.03 (3, J=7.0 Hz, 3H), 0.90 (d, J=6.5 Hz, 3H) ppm.

Step 2: Methyl N-{[(1,1-dimethylpent-4-en-1-yl) amino]carbonyl}-L-valinate

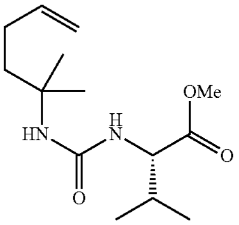

Methyl N-(oxomethylene)-L-valinate (2.80 g, 17.7 mmol) was added to 2-methylhex-5-en-2-amine [*J. Org. Chem.* (1976) 41(5) 855-863.] (2.00 g, 17.7 mmol) in THF (15 mL). After 5 minutes, the reaction mixture was evaporated to give the title compound as a solid, which was triturated with hexane and isolated by filtration (2.71 g). LRMS $(M+H)^+$=271.4.

Step 3: N-{[(1,1-Dimethylpent-4-en-1-yl)amino] carbonyl}-L-valine 1M lithium hydroxide (54 mL, 54 mmol) was added to N-{[(1,1-dimethylpent-4-en-1-yl)amino]carbonyl}-L-valine (2.94 g, 10.9 mmol) in THF (20 mL). The reaction mixture was stirred at RT under nitrogen for 18 hours, then heated to reflux for 2 hours, and cooled to RT. The THF removed by evaporation. Water was then added, and the mixture extracted with DCM (4×). The aqueous layer was made acidic with 1M HCl and extracted with DCM (3×70 mL). The combined organic extracts were dried over anhydrous $Na_2SO_4$ and the solvent evaporated to give the title compound as a white foam (2.25 g). LRMS $(M+H)^+$=257.3.

The following urea intermediates (B51-B52) were prepared using the chemistry described for the preparation of N-{[(1,1-dimethylpent-4-en-1-yl)amino]carbonyl}-L-valine (as described in Intermediate B50), by utilizing the appropriate amino acid and amine.

| Int | Amino Acid | Amine | Structure | Name | LRMS $(M + H)^+$ |
|---|---|---|---|---|---|
| B51 | L-t-Butyl-glycine | N-Methylpent-4-en-1-amine | 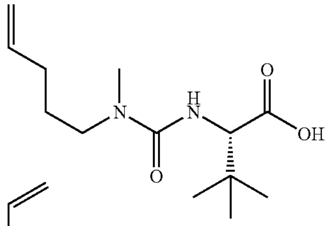 | 3-Methyl-N-{[methyl(pent-4-en-1-yl)amino]carbonyl}-L-valine | 257.3 |
| B52 | L-t-Butyl-glycine | N-Isopropylhex-5-en-1-amine | 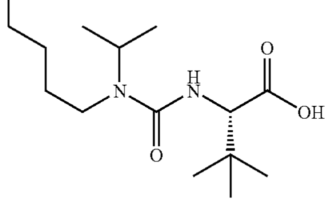 | N-{[Hex-5-en-1-yl(isopropyl)amino] carbonyl}-3-methyl-L-valine | 299.3 |

Intermediate B53: N-Hept-6-enoyl-3-methyl-L-valine

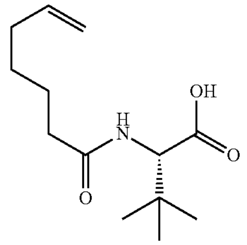

Step 1: Methyl N-Hept-6-enoyl-3-methyl-L-valinate

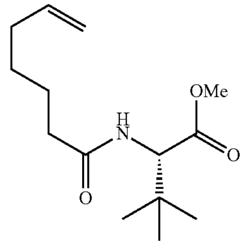

A solution of L-tert-leucine methyl ester (1.00 g, 6.89 mmol), 6-heptenoic acid (1.06 g, 8.26 mmol), EDC (1.58 g, 8.26 mmol) and HOAt (1.23 g, 8.26 mmol) in DMF (10 mL) was stirred at 22° C. for 2 hours. The reaction mixture was diluted with aqueous saturated $NaHCO_3$ (30 mL), and extracted with EtOAc (3×50 mL). The combined organic layers were washed with water (3×30 mL), brine (20 mL), dried over $Na_2SO_4$, filtered and concentrated. The residue was chromatographed on silica gel, eluting with 5-50% EtOAc/hexane, to give the title product (1.42 g, 81%). LRMS (ESI) m/z 256.3 [$(M+H)^+$; calcd for $C_{14}H_{26}NO_3$: 256.2].

Step 2: N-Hept-6-enoyl-3-methyl-L-valine

A solution of methyl N-hept-6-enoyl-3-methyl-L-valinate (1.40 g, 5.48 mmol) in THF (10 mL) and 1N NaOH (10 mL) was stirred at 22° C. for 2 hours. The reaction mixture was acidified to pH 3 with 1 N HCl and extracted with EtOAc (3×150 mL). The combined EtOAc layers were washed with water (50 mL), brine (50 mL), dried over $Na_2SO_4$, filtered and concentrated to give the title product (1.12 g, 84%). LRMS (ESI) m/z 242.3 [$(M+H)^+$; calcd for $C_{13}H_{24}NO_3$: 242.2].

EXAMPLES

Example 1

[(1S,2S)-1-({[2R,4S,7S)-7-cyclohexyl-23-methoxy-12,12-dimethyl-6,9-dioxo-3,4,6,7,8,9,12,13,14,15-decahydro-2H,11H-16,18-etheno-2,5-methanopyrido [2,3-k][1,10,3,6]dioxadiazacyclononadecin-4-yl] carbonyl}amino)-2-vinylcyclopropyl]phosphonic acid

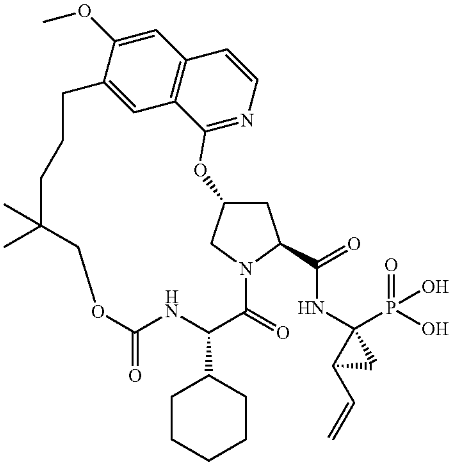

Step 1: (2E)-3-(4-Bromo-3-methoxyphenyl)acrylic acid

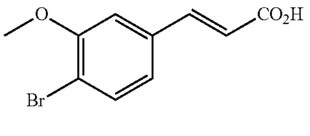

To a solution of 1-bromo-4-iodo-2-methoxybenzene (L. A. Hasvold et al, US 2004/0254159, EXAMPLE 57B) (33.45 g, 107 mmol) in MeCN (100 mL) was added acrylic acid (9.61 g, 133 mmol), $Et_3N$ (37.2 mL, 267 mmol) and palladium acetate (719 mg, 3.2 mmol). The reaction mixture was heated to 90° C. for 40 minutes, cooled to RT and poured into 2.4 L 1M HCl. After stirring for 30 minutes, the solid was filtered, heated to reflux in EtOH (230 mL), allowed to cool to RT and stirred overnight. The solid was filtered and washed with 1:1 EtOH hexane (50 mL) to give desired product. LRMS $ESI^+$ $(M+H)^+$257.0.

Step 2: 7-Bromo-6-methoxyisoquinolin-1(2H)-one

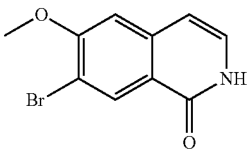

A portion of the product from Step 1 (12.5 g, 48.6 mmol) was azeotroped with benzene and suspended in benzene (94 mL). $Et_3N$ (9.49 mL, 68.1 mmol) and diphenylphosphoryl azide (10.48 mL, 48.6 mmol) were added and the reaction mixture stirred at RT for 1 hour. The mixture was filtered through a pad of silica and eluted with ~1 L of PhMe, the volatiles evaporated, the residue resuspended in diphenylmethane (94 mL) and the mixture heated to reflux for 3 hours (internal temperature 250° C.). The reaction mixture was allowed to cool to RT, stirred overnight, filtered and the solid washed with hexanes (100 mL) to give tan solid (7.4 g). LRMS $ESI^+$ $(M+H)^+$254.1.

Step 3: 7-Bromo-1-chloro-6-methoxyisoquinoline

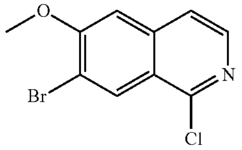

A mixture of the product from Step 2 (7-bromo-6-methoxyisoquinolin-1(2H)-one) (4.7 g, 18.5 mmol) in phosphorus oxychloride (30 mL) was heated to reflux for 2 hours and cooled to RT. The volatiles were then evaporated, and the residue was partitioned between 3 M NaOH and DCM. The organic phase was dried over $Na_2SO_4$; the solvent was evaporated; and the solid was triturated with $Et_2O$ (20 mL) and filtered to give a solid (3.75 g). LRMS $ESI^+$ $(M+H)^+$274.0.

Step 4: Ethyl (4R)-4-[(7-bromo-6-methoxyisoquinolin-1-yl)oxy]-L-prolinate hydrochloride

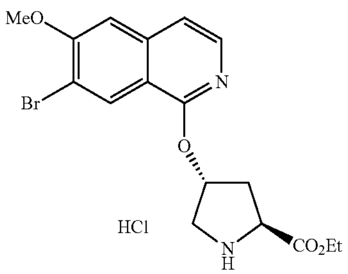

Potassium t-butoxide (618 mg, 5.5 mmol) was added to a stirred solution of BOC trans-4-hydroxyproline (424 mg, 1.83 mmol) in DMSO (10 mL) at RT. The reaction mixture was stirred for 30 minutes, cooled to 15° C. and the product from Step 3 (500 mg, 1.83 mmol) added. The reaction mixture was stirred overnight and partitioned between ice-cold 10% citric acid and EtOAc. The organic phase was washed with water and brine, dried over $Na_2SO_4$ and the solvent evaporated. The crude product was dissolved in EtOH (100 mL), cooled to 0° C., and HCl was bubbled through until saturated. The reaction mixture was allowed to warm to RT and stirred for 24 hours. The volatiles were evaporated and the residue azeotroped with EtOH (×4) to give the title compound as a tan solid (555 mg). LRMS $ESI^-$ $(M+H)^+$395.0.

Step 5: Ethyl (4R)-4-[(7-bromo-6-methoxyisoquinolin-1-yl)oxy]-1-[(2S)-2-cyclohexyl-2-({[(2,2-dimethylpent-4-en-1-yl)oxy]carbonyl}amino)acetyl]-L-prolinate

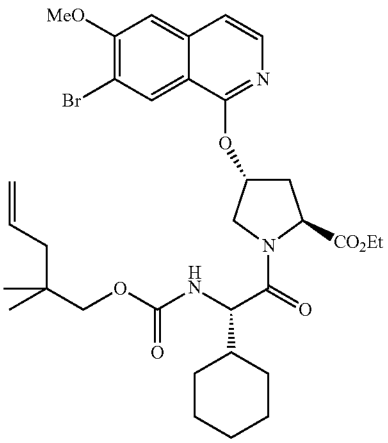

To a solution of the product from step 4 (900 mg, 2.09 mmol) in DMF (10 mL), was added Intermediate B23 (682 mg, 2.29 mmol), DIPEA (1.09 mL, 6.25 mmol) and HATU (1,190 mg, 3.13 mmol), and the reaction mixture stirred for 6 hours at RT. The mixture was then partitioned between EtOAc and 10% $KHSO_4$; the organic phase was washed with brine, dried over $Na_2SO_4$; and the solvent was evaporated. The crude product was purified by chromatography on silica (30-50% EtOAc/hexane) to afford the title compound (1.02 g) as a foam. LRMS $ESI^+$ $(M+H)^+$676.3.

Step 6: Ethyl (4R)-1-[(2S)-2-cyclohexyl-2-({[(2,2-dimethylpent-4-en-1-yl)oxy]carbonyl}amino) acetyl]-4-[(6-methoxy-7-vinylisoquinolin-1-yl)oxy]-L-prolinate

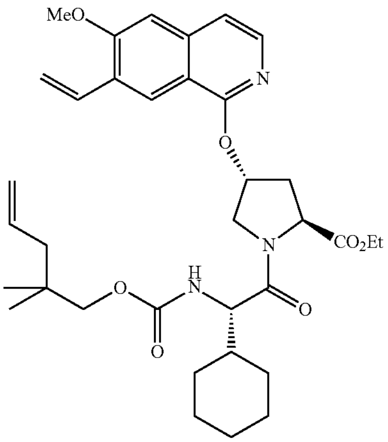

A solution of the product from Step 5 (1.02 g, 1.51 mmol) in PhMe (30 mL) was degassed for 30 minutes by bubbling nitrogen. Tri-n-butylvinyltin (533 μL, 1.81 mmol) and tetrakis(triphenylphosphine)palladium (175 mg, 0.151 mmol) were added, and the reaction mixture was heated to 105° C. for 3 hours, then cooled to RT for 18 hours. The volatiles were evaporated, and the residue was purified by chromatography on silica (20-50% EtOAc/hexane) to afford the title compound (820 mg) as a foam. LRMS ESI$^+$ $(M+H)^+$622.5.

Step 7: Ethyl (2R,4S,7S,14E)-7-cyclohexyl-23-methoxy-12,12-dimethyl-6,9-dioxo-3,4,6,7,8,9,12,13-octahydro-2H,11H-16,18-(ethanediylidene)-2,5-methanopyrido[2,3-k][1,10,3,6]dioxadiazacyclononadecine-4-carboxylate

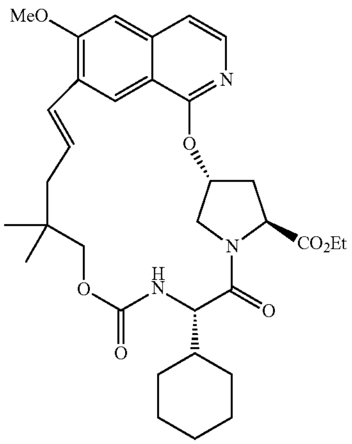

A solution of the product from Step 6 (800 mg, 1.29 mmol) in DCM (200 mL) was degassed for 30 minutes by bubbling nitrogen. Zhan 1B catalyst (189 mg, 0.26 mmol) in degassed DCM (20 mL) was added over 1 hour; the reaction mixture was stirred at RT for 18 hours, then concentrated; and the residue was purified by chromatography on silica (20-50% EtOAc/hexane) to afford the title compound (700 mg) as a foam. LRMS ESI$^+$ $(M+H)^+$594.5.

Step 8: Ethyl (2R,4S,7S)-7-cyclohexyl-23-methoxy-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate

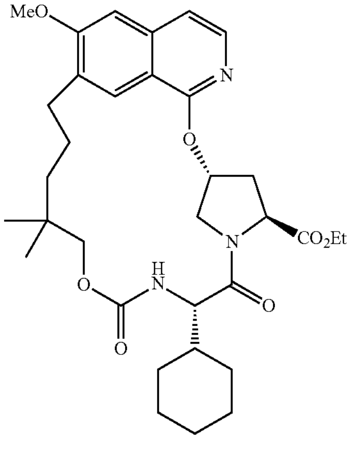

To a solution of the product from Step 7 (600 mg, 1.01 mmol) in EtOAc (50 mL) was added 10% Pd/C (100 mg), and the mixture was hydrogenated under 1 atmosphere of hydrogen for 18 hours. EtOH and additional 10% Pd/C (100 mg) were added, and hydrogenation was continued for 72 hours. The reaction mixture was filtered, and the filtrate was concentrated to afford the title compound (600 mg). LRMS ESI$^+$ $(M+H)^+$596.5.

Step 9: (3R,5S,8S)-8-cyclohexyl-18-methoxy-13,13-dimethyl-7,10-dioxo-2,11-dioxa-6,9,23-triazatetracyclo[15.6.2.1~3,6~0.0~20,24~]hexacosa-1(23),17,19,21,24-pentaene-5-carboxylic acid

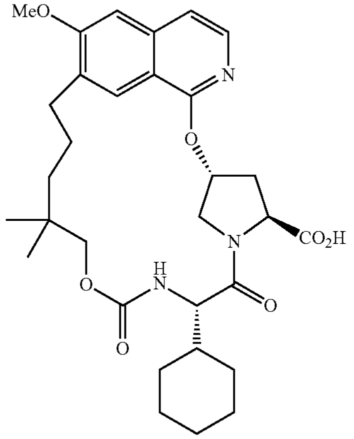

A solution of the product from Step 8 (600 mg, 1.01 mmol) was dissolved in THF (48 mL), water (12 mL) and EtOH (12 mL), and LiOH (169 mg, 7.05 mmol) was added. The reaction mixture was stirred at RT for 18 hours, diluted with 10% aqueous $KHSO_4$, concentrated to remove THF and EtOH and partitioned between water and EtOAc. The organic phase was dried over $Na_2SO_4$, and the solvent was evaporated to afford the title compound (543 mg) as a foam. LRMS ESI$^-$ $(M+H)^+$ 568.4.

Step 10: Diethyl [1-({[(3R,5S,8S)-8-cyclohexyl-18-methoxy-13,13-dimethyl-7,10-dioxo-2,11-dioxa-6,9,23-triazatetracyclo[15.6.2.1~3,6~0.0~20,24~]hexacosa-1(23),17,19,21,24-pentaen-5-yl]carbonyl}amino)-2-vinylcyclopropyl]phosphonate

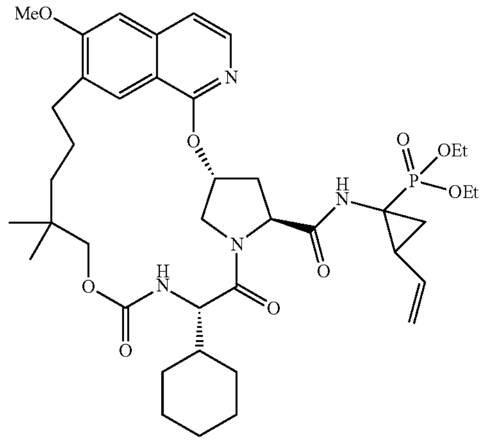

A solution of the product from Step 9 (180 mg, 0.317 mmol) in DMF (2 mL) was treated with Intermediate A1 (77 mg, 0.351 mmol), DIPEA (0.166 mL, 0.95 mmol), DMAP (19 mg, 0.16 mmol) and HATU (145 mg, 0.38 mmol). The reaction mixture was stirred at RT for 18 hours and then directly purified by reverse-phase chromatography (C18 5-100% $CH_3CN$/(water+0.1% TFA)) to give the product (200 mg) as a white foam. LRMS $ESI^+$ $(M+H)^+$769.2.

Step 11: [1-({[(3R,5S,8S)-8-cyclohexyl-18-methoxy-13,13-dimethyl-7,10-dioxo-2,11-dioxa-6,9,23-triaza-tetracyclo[15.6.2.1~3,6~0.0~20,24~]hexacosa-1(23),17,19,21,24-pentaen-5-yl]carbonyl}amino)-2-vinylcyclopropyl]phosphonic acid

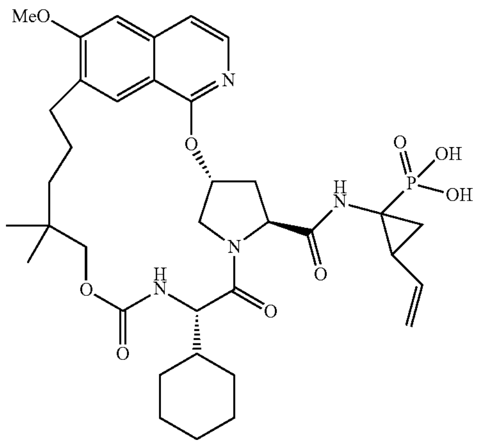

To a solution of the product from Step 10 (100 mg, 0.13 mmol) in $CH_3CN$ (5 mL) at 0° C., was added 2,6-lutidine (0.042 mL, 0.36 mmol) followed by iodotrimethylsilane (0.05 mL, 0.36 mmol). Three additional portions of iodotrimethylsilane (0.05 mL, 0.36 mmol) were added at 1 hour intervals, and the reaction mixture then was stirred at RT for 18 hours. MeOH (0.5 mL) and $Et_3N$ (0.2 mL) were added; the volatiles were evaporated; and the residue was dissolved in DMSO and purified by reverse-phase chromatography (C18 5-100% $CH_3CN$/(water+0.1% TFA)) to give the product (200 mg) as a white foam. LRMS $ESI^+$ $(M+H)^+$.

By utilizing the appropriate Intermediates A and B, the following compounds may be prepared in a similar fashion:

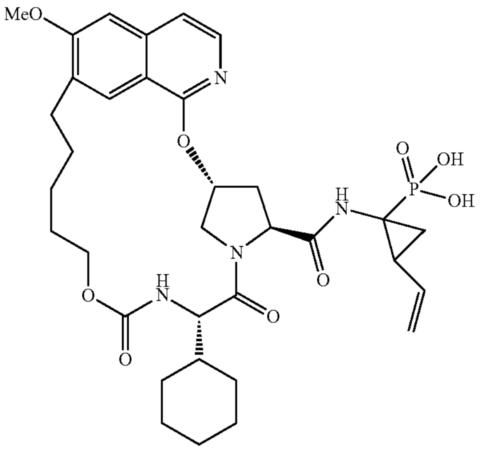

-continued

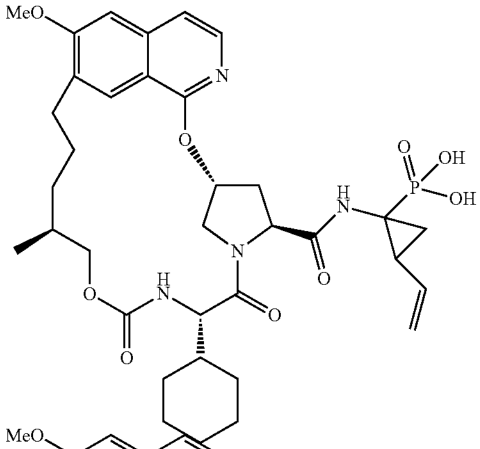

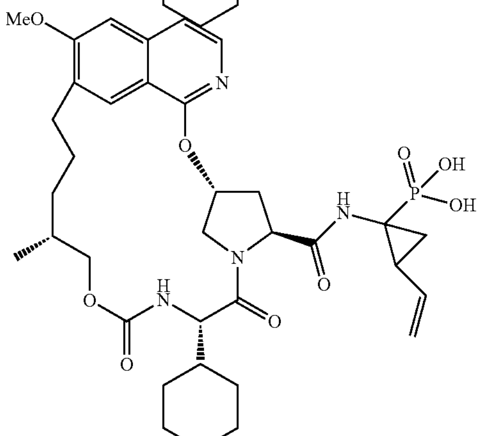

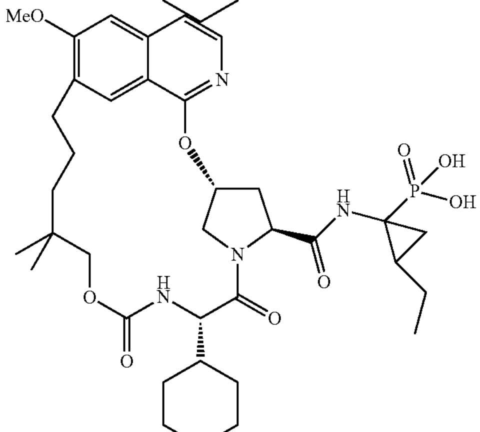

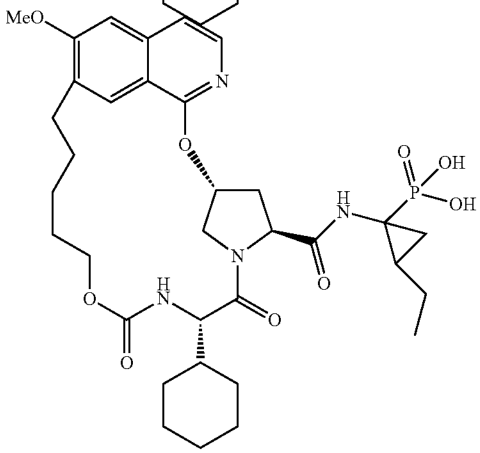

-continued
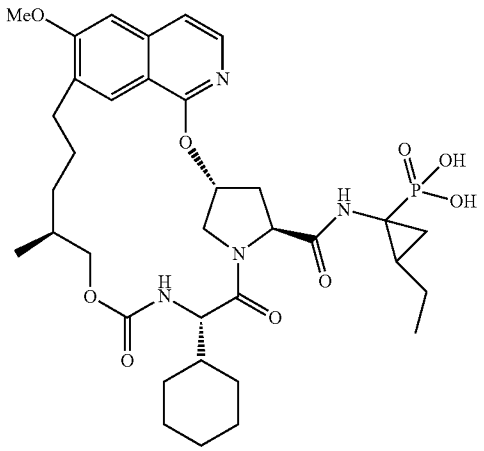
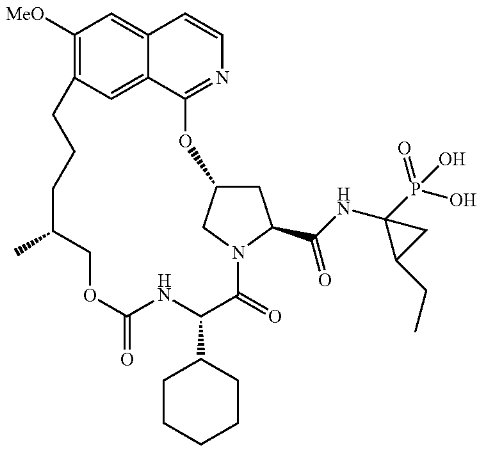
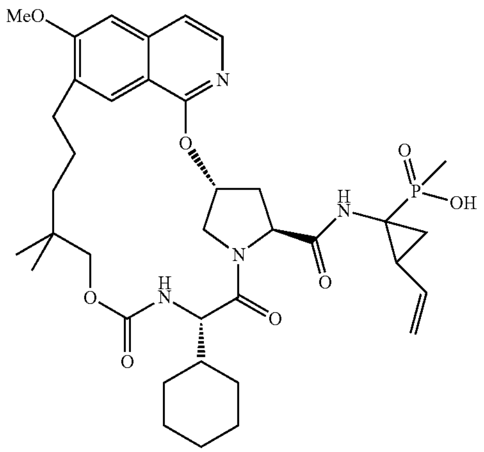
-continued
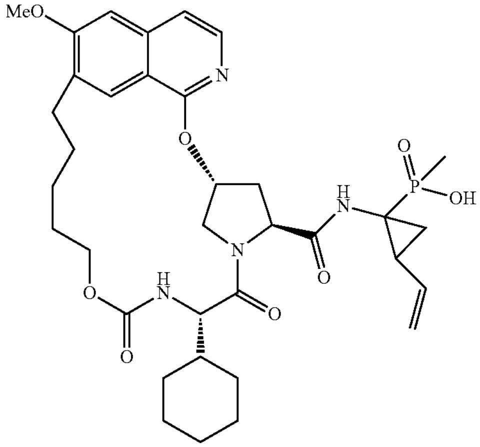
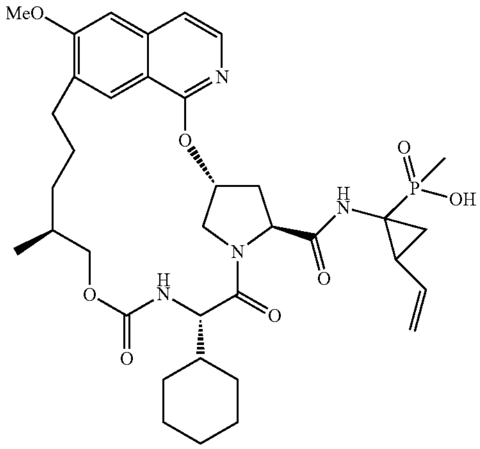
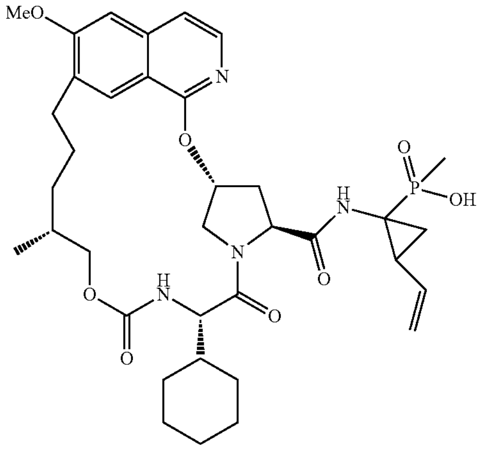

-continued
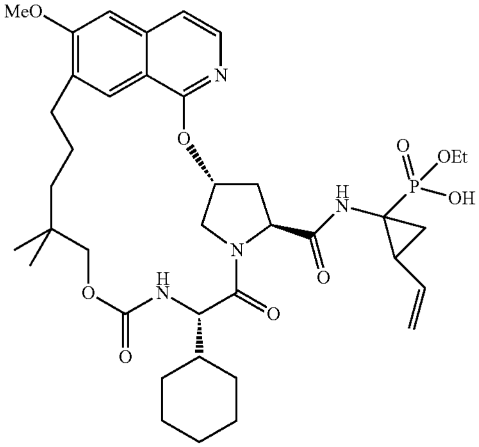
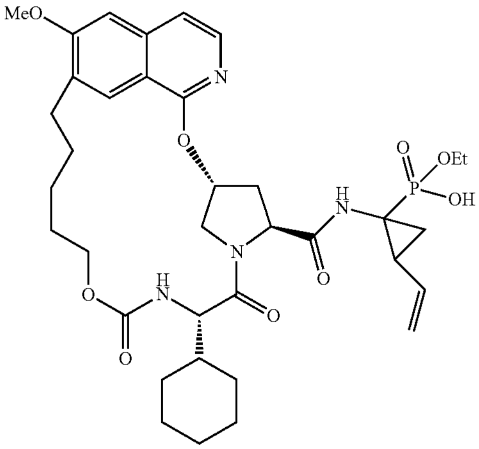
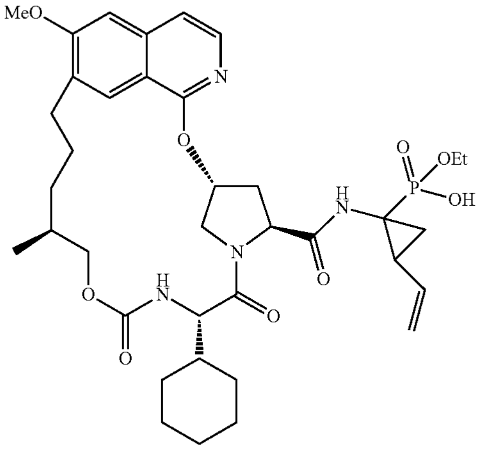
-continued
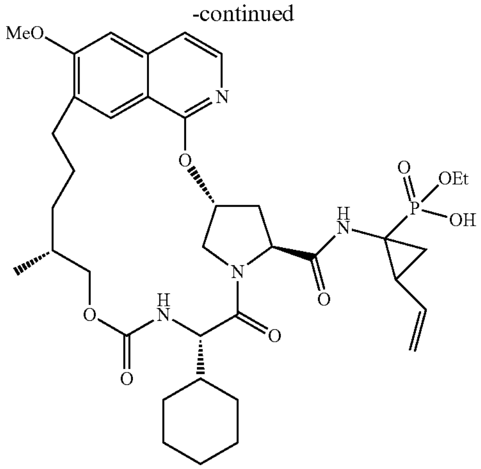
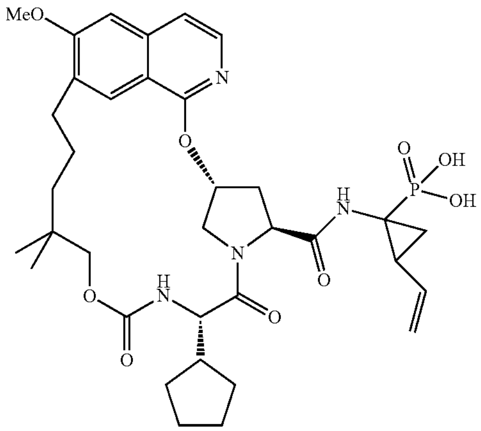
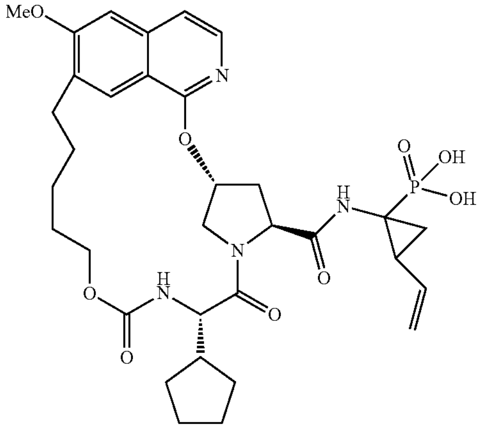
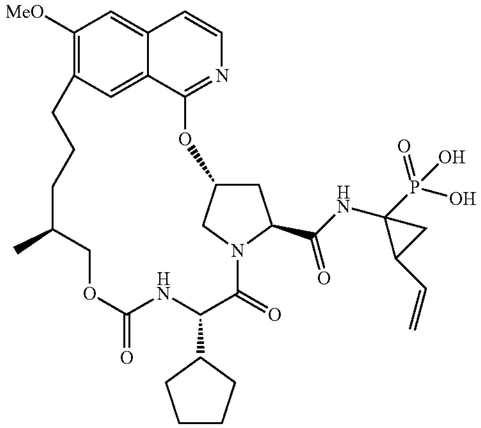

-continued
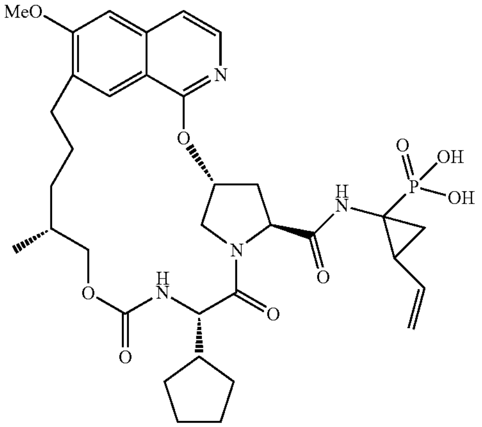
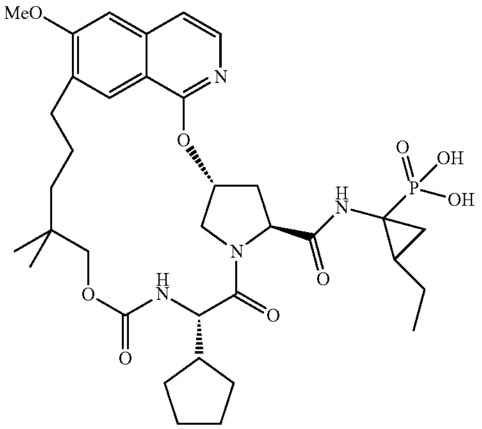
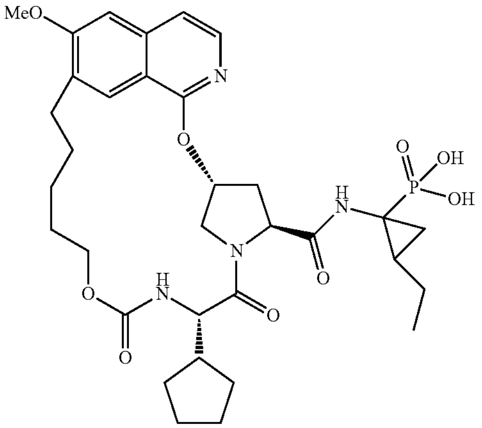
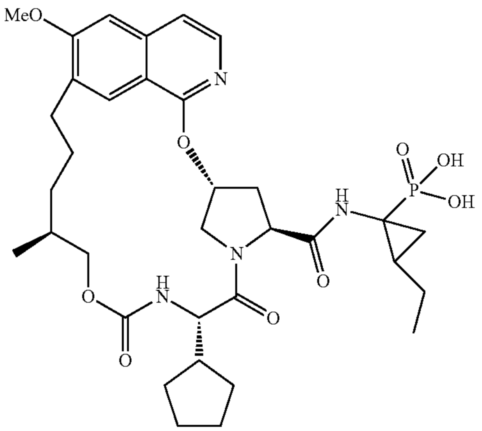
-continued
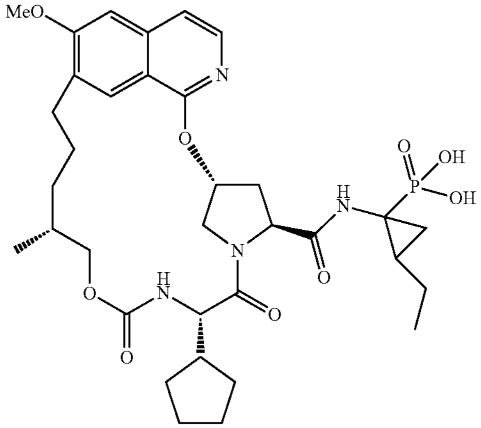
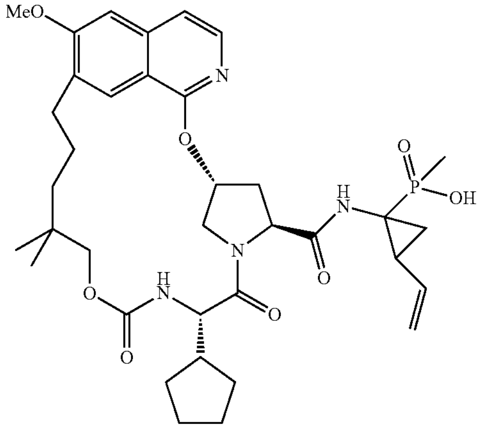
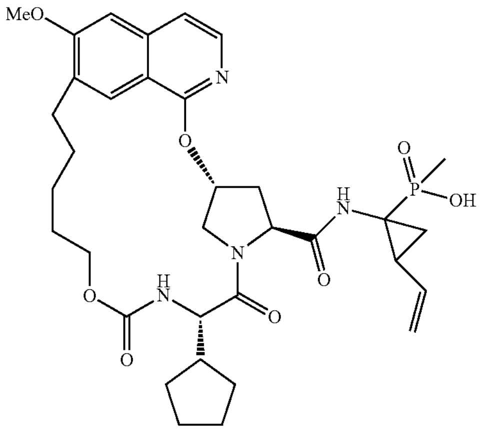
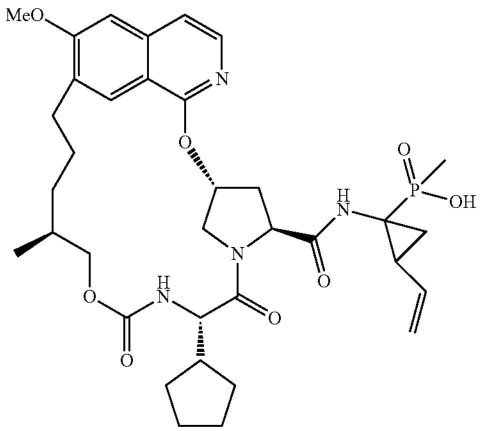

-continued
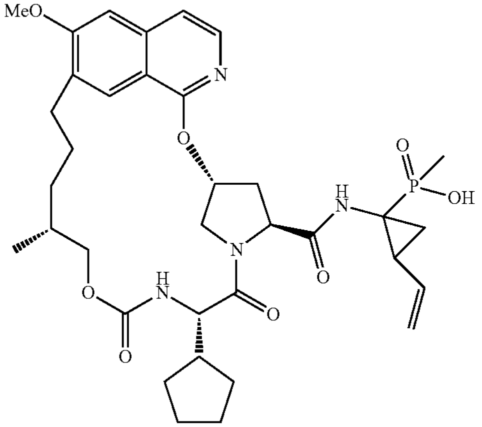
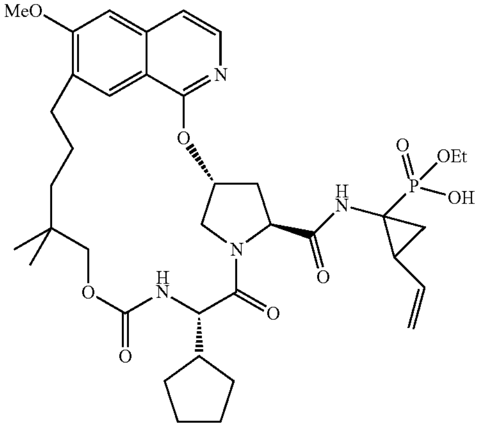
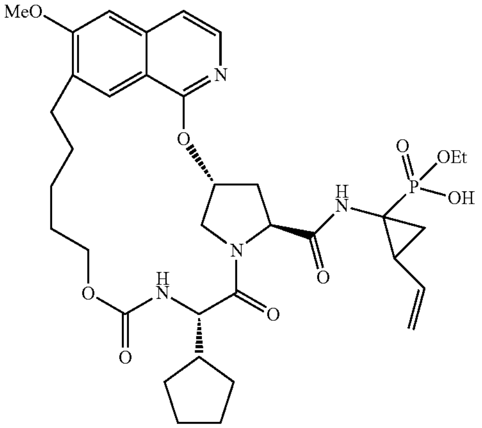
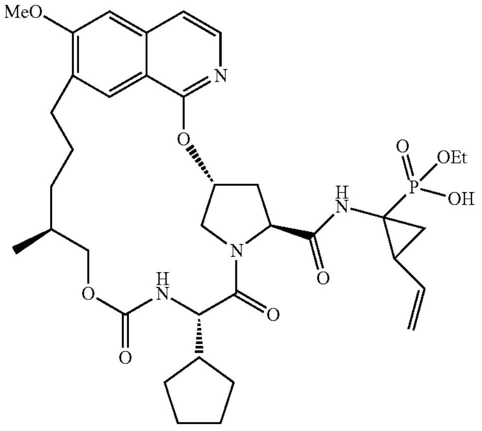
-continued
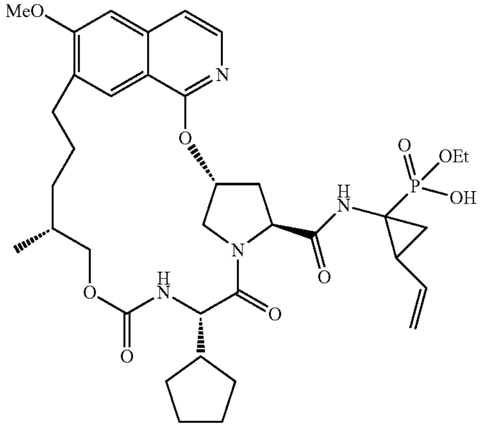
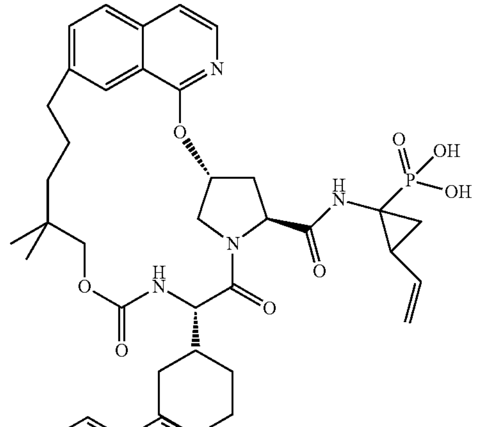
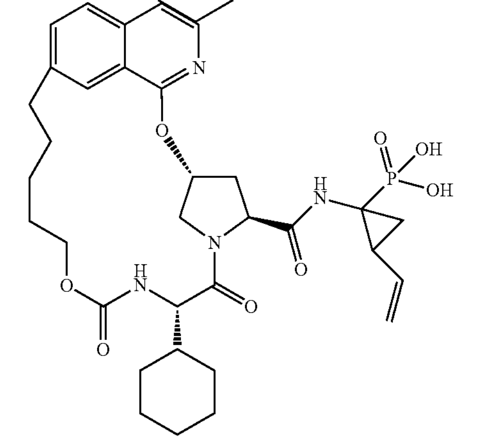
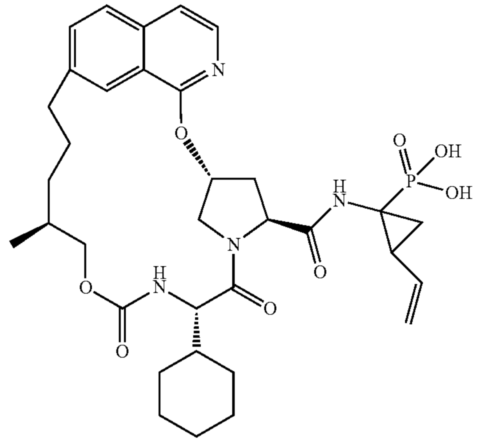

-continued
-continued
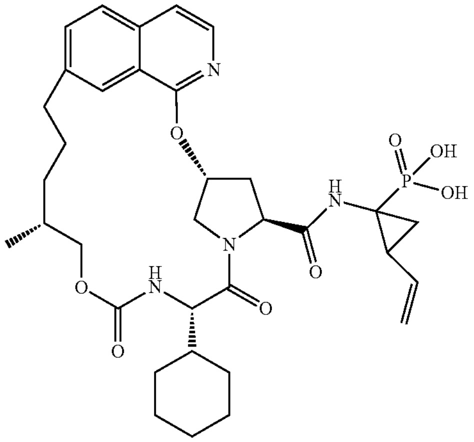
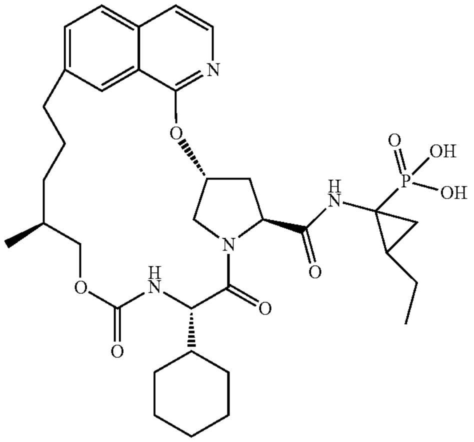
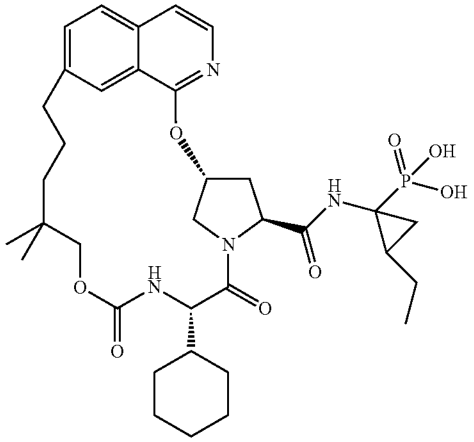
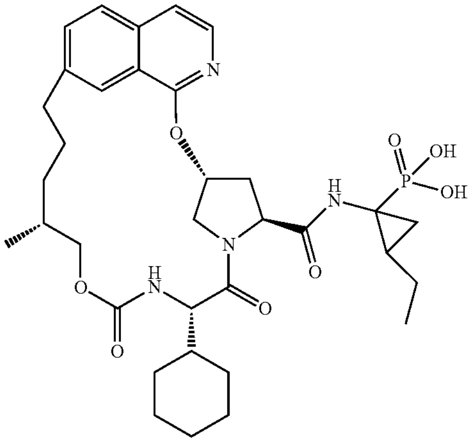
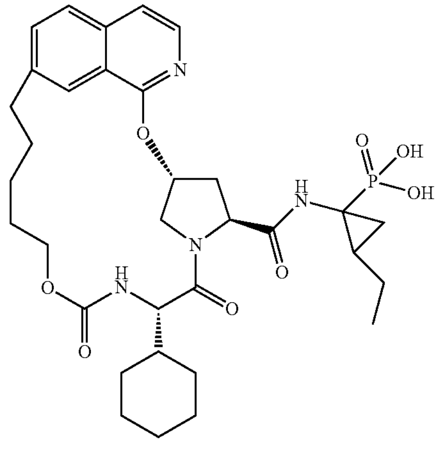
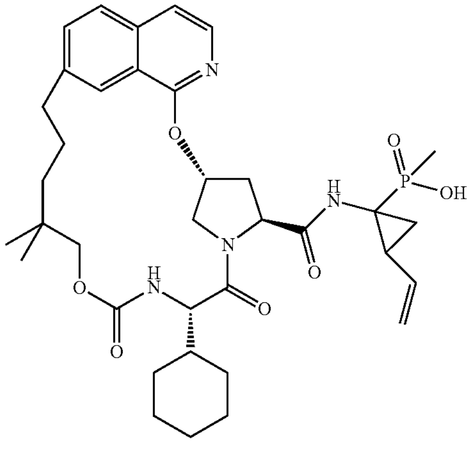

-continued
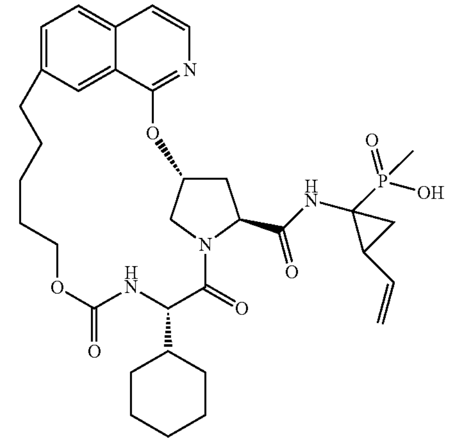
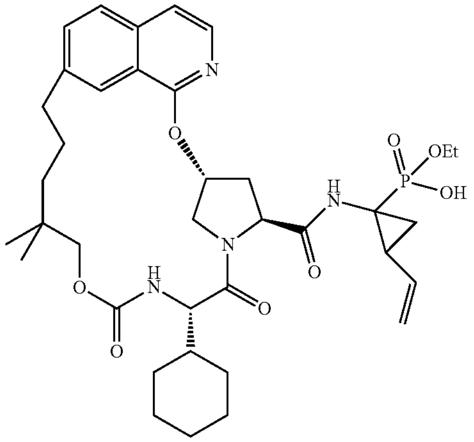
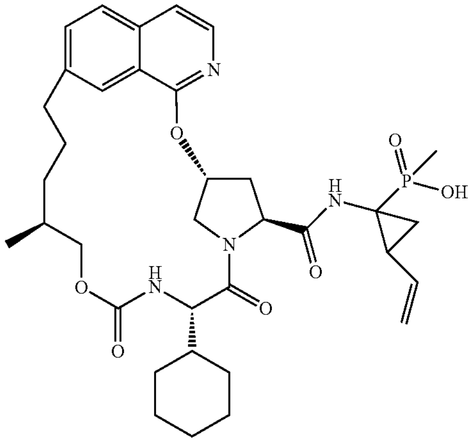
-continued
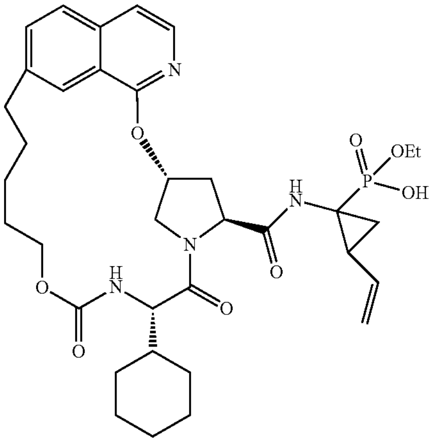
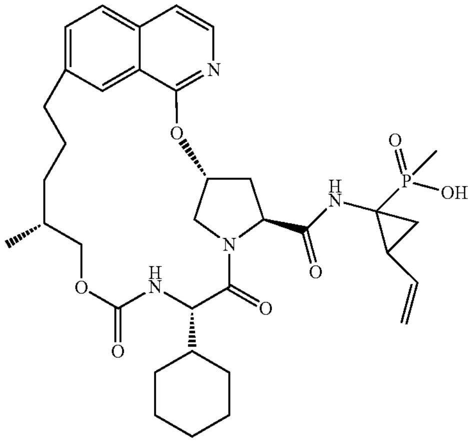
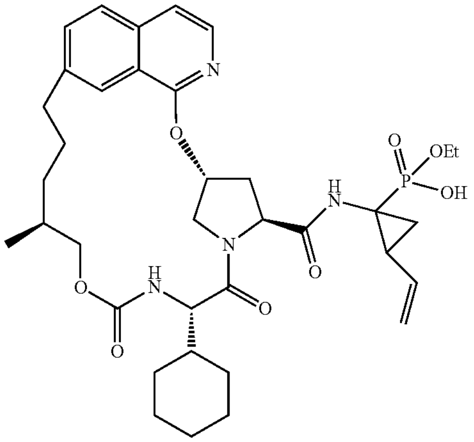

-continued
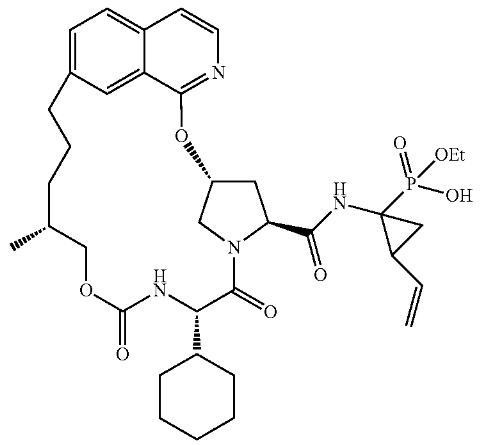
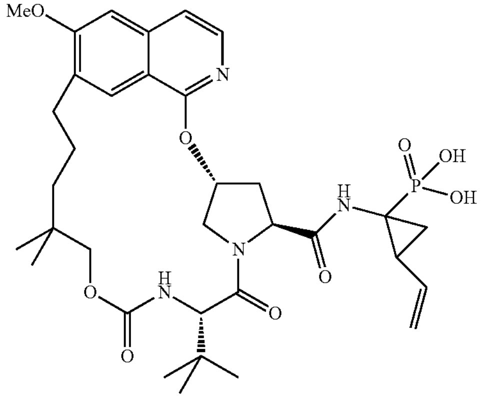
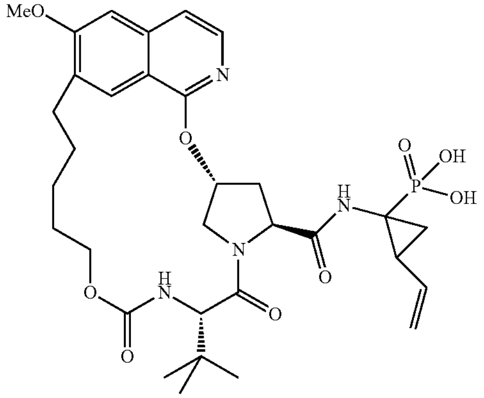
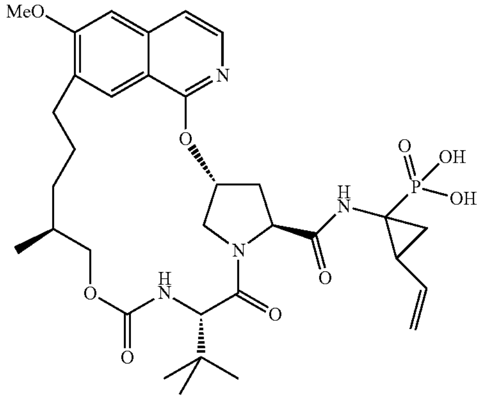
-continued
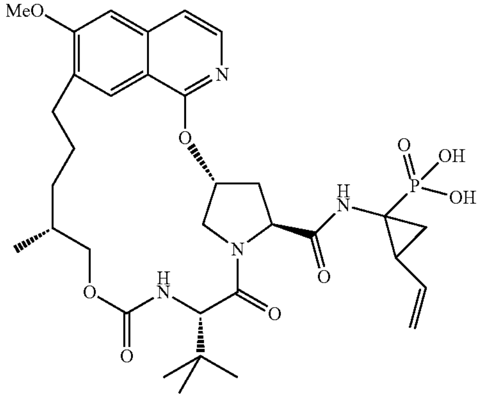
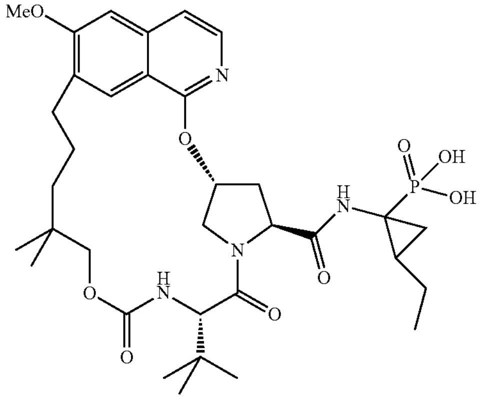
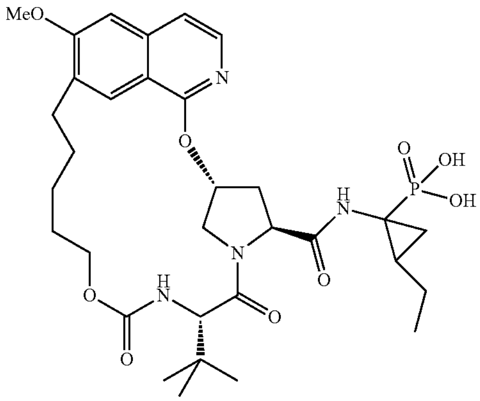
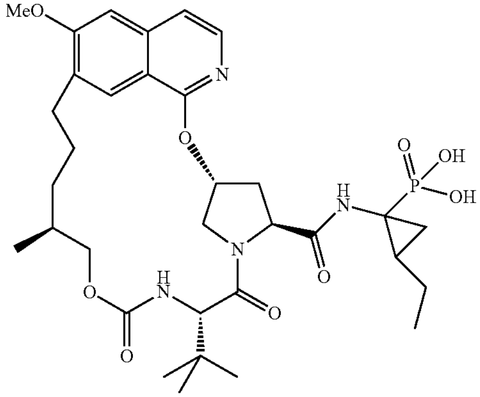

-continued
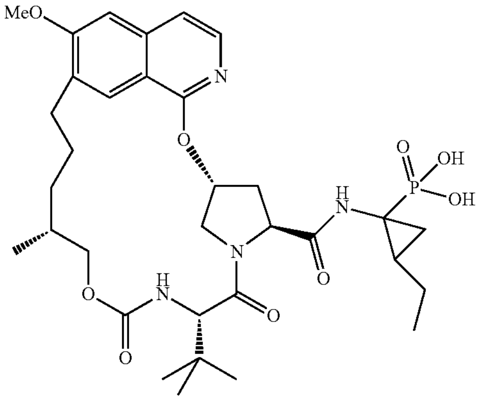
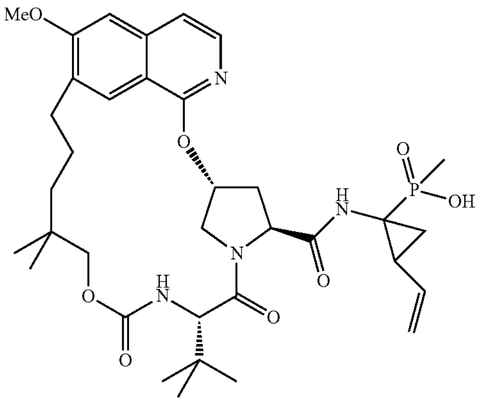
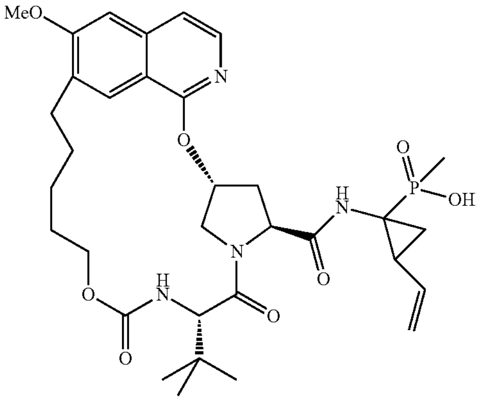
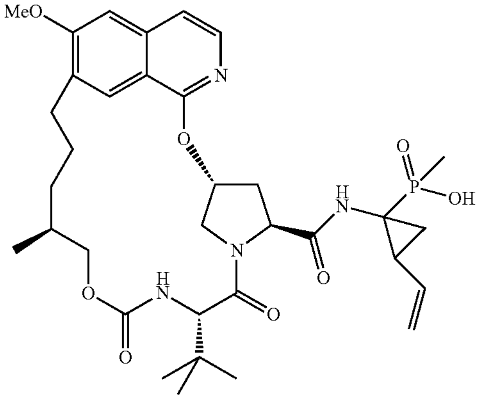
-continued
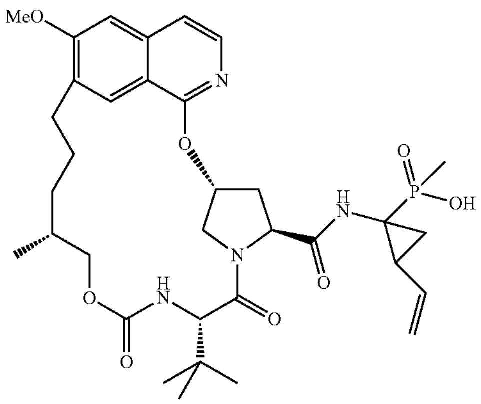
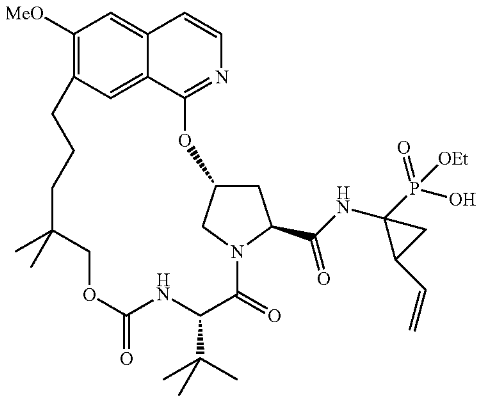
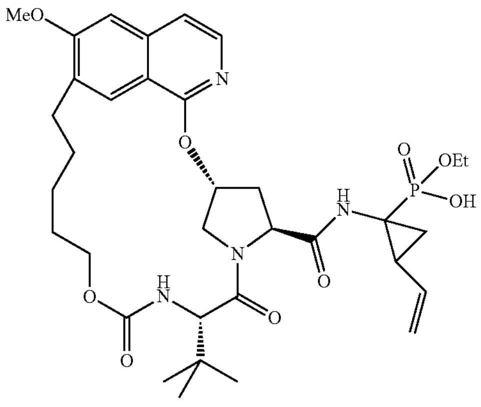
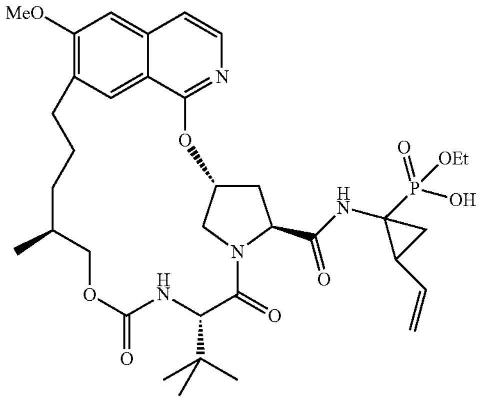

-continued

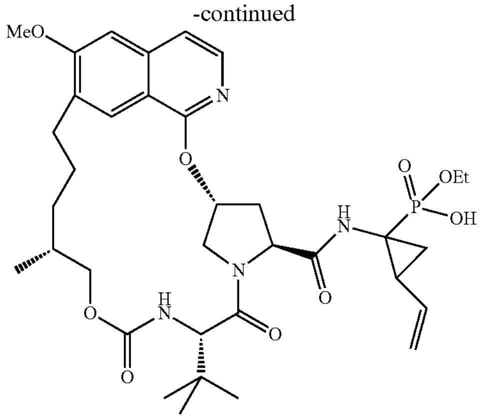

What is claimed is:

1. A compound of formula (I):

(I)

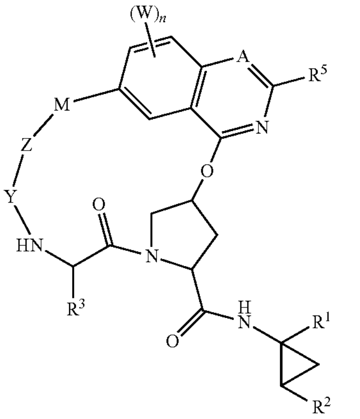

or a pharmaceutically acceptable salt thereof, wherein:

n is 1 or 2;

$R^1$ is —CONHP(O)$R^{11}R^{12}$, or —P(O)$R^{11}R^{12}$;

$R^2$ is $C_1$-$C_6$ alkyl, $C_2$-$C_6$ alkenyl or $C_3$-$C_8$ cycloalkyl, wherein said alkyl, alkenyl or cycloalkyl is optionally substituted with 1 to 3 halo;

$R^3$ is $C_1$-$C_8$ alkyl, $C_3$-$C_8$ cycloalkyl, $C_3$-$C_8$ cycloalkyl($C_1$-$C_8$)alkyl, aryl($C_1$-$C_8$)alkyl, or Het, wherein aryl is phenyl or naphthyl and said alkyl, cycloalkyl, or aryl is optionally substituted with 1 to 3 substituents selected from the group consisting of halo, —$OR^{10}$, —$SR^{10}$)$_2$, —N($R^{10}$)$_2$, —N($C_1$-$C_6$ alkyl)O($C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2$($C_1$-$C_6$ alkyl), —S(O)($C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, —C(O)$R^{10}$, and —CON($R^{10}$)$_2$; Het is a 5- to 6-membered saturated cyclic ring having 1, 2 or 3 heteroatoms selected from N, O and S, wherein said ring is optionally substituted with 1 to 3 substituents selected from the group consisting of halo, —$OR^{10}$, —$SR^{10}$, —N($R_{10}$)$_2$, —N($C_1$-$C_6$ alkyl)O($C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2$($C_1$-$C_6$ alkyl), —S(O)($C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, —C(O)$R^{10}$, and —CON($R^{10}$)$_2$;

$R^4$ is H, $C_1$-$C_8$ alkyl, $C_3$-$C_8$ cycloalkyl($C_1$-$C_8$)alkyl, or aryl ($C_1$-$C_8$)alkyl; wherein aryl is phenyl or naphthyl and said alkyl, cycloalkyl, or aryl is optionally substituted with 1 to 3 substituents selected from the group consisting of halo, —$OR^{10}$, —$SR^{10}$, —N($R^{10}$)$_2$, —N($C_1$-$C_6$ alkyl)O($C_1$-$C_6$ alkyl), $C_1$-$C_6$ alkyl, $C_1$-$C_6$ haloalkyl, halo ($C_1$-$C_6$ alkoxy), —$NO_2$, —CN, —$CF_3$, —$SO_2$($C_1$-$C_6$ alkyl), —S(O)($C_1$-$C_6$ alkyl), —$NR^{10}SO_2R^6$, —$SO_2N$ ($R^6$)$_2$, —$NHCOOR^6$, —$NHCOR^6$, —$NHCONHR^6$, —$CO_2R^{10}$, —C(O)$R^{10}$, and —CON($R^{10}$)$_2$;

$R^5$ is H, halo, —OH, $C_1$-$C_6$ alkoxy, $C_1$-$C_6$ alkyl, —CN, —$CF_3$, —$SR^{10}$, —$SO_2$($C_1$-$C_6$ alkyl), $C_3$-$C_8$ cycloalkyl, $C_3$-$C_8$ cycloalkoxy, $C_1$-$C_6$ haloalkyl, —N($R^7$)$_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, —$OR^{10}$, —$SR^{10}$, —N($R^7$)$_2$, —N($C_1$-$C_6$ alkyl)O($C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, —$NO_2$, —CN, —$CF_3$, —$SO_2$($C_1$-$C_6$ alkyl), —$NR^{10}SO_2R^6$, —$SO_2N(R^6)_2$, —S(O)($C_1$-$C_6$ alkyl), —$NHCOOR^6$, —$NHCOR^6$, —$NHCONHR^6$, —$CO_2R^{10}$, —C(O)$R^{10}$, and —CON($R^{10}$)$_2$; wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^6$ is $C_1$-$C_8$ alkyl, $C_3$-$C_8$ cycloalkyl, $C_3$-$C_8$ cycloalkyl($C_1$-$C_5$)alkyl, aryl, aryl($C_1$-$C_4$)alkyl, heteroaryl, heteroaryl ($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W' substituents or aryl is substituted by —P(O)$R^{11}R^{12}$; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Y is —C(═O)—, —$SO_2$—, or —C(═N—CN)—;

Z is)-C($R^{10}$)$_2$—, —O—, or —N($R^4$)—;

M is $C_1$-$C_{12}$ alkylene or $C_2$-$C_{12}$ alkenylene or $C_2$-$C_{12}$ alkynylene, wherein said alkylene or alkenylene is optionally substituted with 1, 2 or 3 substituents selected from the group consisting of $C_1$-$C_8$ alkyl, $C_3$-$C_8$ cycloalkyl ($C_1$-$C_8$ alkyl), and aryl($C_1$-$C_8$ alkyl); wherein 2 substituents on adjacent carbon atoms of M are optionally taken together to form a 3- to 6-membered cyclic ring containing 0 to 3 heteroatoms selected from N, O and S, or 2 substituents on the same carbon atom of M are optionally taken together to form a 3- to 6-membered cyclic ring containing 0 to 3 heteroatoms selected from N, O and S;

A is —C($R^{16}$)— or —N—;

when $R^5$ is other than H, $R^{16}$ is H, $C_1$-$C_6$ alkyl, halo, —$OR^{10}$, —$SR^{10}$, or —N($R^{10}$)$_2$;

when $R^5$ is H, $R^{16}$ is H, $C_1$-$C_6$ alkyl, halo, —OH, $C_1$-$C_6$ alkoxy, —CN, —$CF_3$, —$SR^{10}$, —$SO_2$($C_1$-$C_6$ alkyl), $C_3$-$C_8$ cycloalkyl, $C_3$-$C_8$ cycloalkoxy, $C_1$-$C_6$ haloalkyl, —$N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, —$OR^{10}$, —$SR^{10}$, —$N(R^7)_2$, —$N(C_1$-$C_6$ alkyl)O($C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, —$NO_2$, —CN, —$CF_3$, —$SO_2$($C_1$-$C_6$ alkyl), —$NR^{10}SO_2R^6$, —$SO_2N(R^6)_2$, —S(O)($C_1$-$C_6$ alkyl), —$NHCOOR^6$, —$NHCOR^6$, —$NHCONHR^6$, —$CO_2R^{10}$, —$C(O)R^{10}$, and —$CON(R^{10})_2$; wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

or $R^5$ and $R^{16}$ are optionally taken together to form a 5- to 6-membered saturated, unsaturated non-aromatic, or aromatic cyclic ring having 0 to 2 heteroatoms selected from N, O and S;

each $R^7$ is independently H, $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W' substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently H, halo, —$OR^7$, $C_1$-$C_6$ alkyl, —CN, —$CF_3$, —$NO_2$, —$SR^7$, —$CO_2R^7$, —$CON(R^7)_2$, —$C(O)R^7$, —$N(R^{10})C(O)R^7$, —$SO_2$($C_1$-$C_6$ alkyl), —S(O)($C_1$-$C_6$ alkyl), $C_3$-$C_8$ cycloalkyl, $C_3$-$C_8$ cycloalkoxy, $C_1$-$C_6$ haloalkyl, —$N(R^7)_2$, —$N(C_1$-$C_6$ alkyl)O($C_1$-$C_6$ alkyl), halo($C_1$-$C_6$ alkoxy), —$NR^{10}SO_2R^7$, —$SO_2N(R^7)_2$, —$NHCOOR^7$, —$NHCONHR^7$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein 2 adjacent W moieties are optionally taken together with the atoms to which they are attached to form a 5- to 6-membered saturated, unsaturated non-aromatic, or aromatic cyclic ring having 0 to 2 heteroatoms selected from N, O and S;

each W' is independently H, halo, —$OR^{10}$, $C_1$-$C_6$ alkyl, —CN, —$CF_3$, —$NO_2$, —$SR^{10}$, —$CO_2R^{10}$, —$CON(R^{10})_2$, —$C(O)R^{10}$, —$N(R^{10})C(O)R^{10}$, —$SO_2$ ($C_1$-$C_6$ alkyl), —S(O)($C_1$-$C_6$ alkyl), $C_3$-$C_8$ cycloalkyl, $C_3$-$C_8$ cycloalkoxy, $C_1$-$C_6$ haloalkyl, —$N(R^{10})_2$, —$N(C_1$-$C_6$ alkyl)O($C_1$-$C_6$ alkyl), halo($C_1$-$C_6$ alkoxy), —$NR^{10}SO_2R^{10}$, —$SO_2N(R^{10})_2$, —$NHCOOR^{10}$, —$NHCONHR^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein 2 adjacent W' moieties are optionally taken together with the atoms to which they are attached to form a 5- to 6-membered saturated, unsaturated non-aromatic, or aromatic cyclic ring having 0 to 2 heteroatoms selected from N, O and S;

each $R^{10}$ is independently H or $C_1$-$C_6$ alkyl;

each $R^{11}$ is independently $C_1$-$C_6$ alkyl, —$OR^{13}$, —$N(R^{10}$-V-$CO_2R^{10}$, —O-V-$CO_2R^{10}$, —S-V-$CO_2R^{10}$, —$N(R^{10})(R^{13})$, $R^{14}$, or —$N(R^{10})SO_2R^6$;

each $R^{12}$ is independently —$OR^{13}$, —$N(R^{10})$-V-$CO_2R^{10}$, —O-V-$CO_2R^{10}$, —S-V-$CO_2R^{10}$, or —$N(R^{10}$ $(R^{13})$;

or $R^{11}$ and $R^{12}$ are optionally taken together, with the phosphorus atom to which they are attached, to form a 5- to 7-membered monocyclic ring;

each V is independently —$CH(R^{15})$ or $C_1$-$C_4$ alkylene-CH$(R^{15})$;

each $R^{13}$ is independently H, $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of aryl, aryl ($C_1$-$C_4$ alkyl), $C_3$-$C_8$ cycloalkyl, $C_3$-$C_8$ cycloalkyl($C_1$-$C_4$ alkyl), heteroaryl, heteroaryl($C_1$-$C_4$ alkyl), heterocyclyl, heterocyclyl($C_1$-$C_4$ alkyl), $C_1$-$C_6$ alkyl, halo, —$OC(O)OR^6$, —$OC(O)R^6$, —$OR^{10}$, —$SR^{10}$, —$N(R^{10})_2$, —$C(O)R^{10}$, —$NO_2$, —CN, —$CF_3$, —$SO_2$ ($C_1$-$C_6$ alkyl), —S(O)($C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, and —$C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^{14}$ is $C_6$ alkyl, $C_2$-$C_6$ alkenyl, aryl or heteroaryl, wherein aryl is phenyl or naphthyl, and heteroaryl is independently a 5- or 6-membered aromatic ring having 1, 2 or 3 heteroatoms selected from N, O and S, attached through a ring carbon or nitrogen, and wherein said aryl or heteroaryl is optionally substituted with 1 to 2 substituents selected from the group consisting of $C_1$-$C_6$ alkyl, halo, —$OC(O)OR^6$, —$OC(O)R^6$, —$OR^{10}$, —$SR^{10}$, —$N(R^{10})_2$, —$C(O)R^{10}$, —$NO_2$, —CN, —$CF_3$, —$SO_2$($C_1$-$C_6$ alkyl), —S(O)($C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, and —$C(O)N(R^{10})_2$; and each $R^{15}$ is independently $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of $C_1$-$C_6$ alkyl, halo, —OC(O)OR$^6$, —OC(O)R$^6$, —OR$^{10}$, —N(R$^{10}$)$_2$, —C(O)R$^{10}$, —NO$_2$, —CN, —CF$_3$, —SO$_2$(C$_1$-C$_6$ alkyl), —S(O)(C$_1$-C$_6$ alkyl), —NR$^{10}$SO$_2$R$^6$, —SO$_2$N(R$^6$)$_2$, —NHCOOR$^6$, —NHCOR$^6$, —NH-CONHR$^6$, —CO$_2$R$^{10}$, and)-C(O)N(R$_{10}$)$_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S.

2. A compound of claim 1, wherein n is 1.

3. A compound of claim 1, wherein R$^1$ is —P(O)R$^{11}$R$^{12}$.

4. A compound of claim 3, wherein R$^{11}$ is independently C$_1$-C$_6$ alkyl, or —OR$^{13}$, and R$^{12}$ is independently —OR$^{13}$.

5. A compound of claim 4, wherein R$^{13}$ is H or C$_1$-C$_6$ alkyl.

6. A compound of claim 4, wherein R$^{11}$ is selected from the group consisting of —OCH$_2$CH$_3$, —CH$_3$, and —OH, and R$^{12}$ is —OH.

7. A compound of claim 1, wherein R$^2$ is C$_1$-C$_6$ alkyl or C$_2$-C$_6$ alkenyl.

8. A compound of claim 7, wherein R$^2$ is —CH=CH$_2$ or —CH$_2$CH$_3$.

9. A compound of claim 1, wherein R$^3$ is C$_1$-C$_8$ alkyl or C$_3$-C$_g$ cycloalkyl.

10. A compound of claim 9, wherein R$^3$ is —C(CH$_3$)$_3$, cyclohexyl or cyclopentyl.

11. A compound of claim 1, wherein R$^5$ is H, Z is —O—, and Y is —C(=O)—.

12. A compound of claim 1, wherein W is H or —O—C$_1$-C$_6$ alkyl.

13. A compound of claim 12, wherein W is H or —OCH$_3$.

14. A compound of claim 1, wherein A is —C(R$^{16}$)—.

15. A compound of claim 14, wherein R$^{16}$ is H.

16. A compound of claim 1, wherein M is C$_1$-C$_{12}$ alkylene wherein said alkylene is optionally substituted with 1 or 2 substituents selected from the group consisting of C$_1$-C$_8$ alkyl.

17. A compound of claim 16, wherein M is selected from the group consisting of —(CH$_2$)$_5$—, —(CH$_2$)$_3$CH(CH$_3$)CH$_2$—, and —(CH$_2$)$_3$C(CH$_3$)$_2$CH$_2$—.

18. A pharmaceutical composition comprising an effective amount of a compound of claim 1, and a pharmaceutically acceptable carrier.

19. A pharmaceutical composition of claim 18, further comprising a second therapeutic agent selected from the group consisting of a HCV antiviral agent, an immunomodulator, and an anti-infective agent.

20. A method of manufacturing a medicament for preventing or treating infection by HCV in a subject in need thereof, said method comprising providing a compound of formula (I):

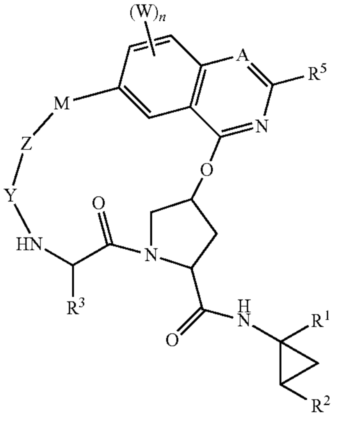

(I)

or a pharmaceutically acceptable salt and/or hydrate thereof, wherein:

n is 1 or 2;

R$^1$ is —CONHP(O)R$^{11}$R$^{12}$, or —P(O)R$^{11}$R$^{12}$;

R$^2$ is C$_1$-C$_6$ alkyl, C$_2$-C$_6$ alkenyl or C$_3$-C$_8$ cycloalkyl, wherein said alkyl, alkenyl or cycloalkyl is optionally substituted with 1 to 3 halo;

R$^3$ is C$_1$-C$_8$ alkyl, C$_3$-C$_8$ cycloalkyl, C$_3$-C$_8$ cycloalkyl(C$_1$-C$_8$)alkyl, aryl(C$_1$-C$_8$)alkyl, or Het wherein a 1 is phenyl or naphthyl and said alkyl cycloalkyl or aryl is optionally substituted with 1 to 3 substituents selected from the group consisting of halo, —OR$^{10}$, —SR$^{10}$, —N(R$^{10}$)$_2$, —N(C$_1$-C$_6$ alkyl)O(C$_1$-C$_6$ alkyl), C$_1$-C$_6$ alkyl, C$_1$-C$_6$ haloalkyl, halo(C$_1$-C$_6$ alkoxy), —NO$_2$, —CN, —CF$_3$, —SO$_2$1-C$_6$ alkyl), —S(O)(C$_1$-C$_6$ alkyl), —NR$^{10}$SO$_7$R$^6$—SO$_2$N(R$^6$)$_2$, —NHCOOR$^6$, —NH-COR$^6$, —NHCONHR$^6$, —CO$_2$R$^{10}$, —C(O)R$^{10}$, and —CON(R$^{10}$)$_2$; Het is a 5- to 6-membered saturated cyclic ring having 1, 2 or 3 heteroatoms selected from N, O and S, wherein said ring is optionally substituted with 1 to 3 substituents selected from the group consisting of halo, —OR$^{10}$, —SR$^{10}$, —N(R$^{10}$)$_2$, —N(C$_1$-C$_6$ alkyl)O(C$_1$-C$_6$ alkyl), C$_1$-C$_6$ alkyl, C$_1$-C$_6$ haloalkyl, halo(C$_1$-C$_6$ alkoxy), —NO$_2$, —CN, —CF$_3$, —SO$_2$(C$_1$-C$_6$ alkyl), —S(O)(C$_1$-C$_6$ alkyl), —NR$^{10}$SO$_2$R$^6$—SO$_2$N(R$^6$)$_2$, —NHCOOR$^6$, —NHCOR$^6$, —NHCONHR$^6$, —CO$_2$R$^{10}$, —C(O)R$^{10}$, and)-CON(R$^{10}$)$_2$;

R$^4$ is H, C$_1$-C$_8$ alkyl, C$_3$-C$_8$ cycloalkyl(C$_1$-C$_8$)alkyl, or aryl(C$_1$-C$_8$)alkyl; wherein aryl is phenyl or naphthyl and said alkyl, cycloalkyl, or aryl is optionally substituted with 1 to 3 substituents selected from the group consisting of halo, —OR$^{10}$, —SR$^{10}$, —N(R$^{10}$)$_2$, —N(C$_1$-C$_6$ alkyl)O(C$_1$-C$_6$ alkyl), C$_1$-C$_6$ alkyl, C$_1$-C$_6$ haloalkyl, halo(C$_1$-C$_6$ alkoxy), —NO$_2$—CN, —CF$_3$, —SO$_2$(C$_1$-C$_6$ alkyl), —S(O)(C$_1$-C$_6$ alkyl), —NR$^{10}$SO$_2$R$^6$ —SO$_2$N(R$^6$)$_2$, —NHCOOR$^6$, —NHCOR$^6$, —NHCONHR$^6$, —CO$_2$R$^{10}$, —C(O)R$^{10}$, and —CON(R$^{10}$)$_2$;

R$^5$ is H, halo, —OH, C$_1$-C$_6$ alkoxy, C$_1$-C$_6$ alkyl, —CN, —CF$_3$, —SR$^{10}$, —SO$_2$(C$_1$-C$_6$ alkyl), C$_3$-C$_8$ cycloalkyl, C$_3$-C$_8$ cycloalkoxy, C$_1$-C$_6$ haloalkyl, —N(R$^7$)$_7$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, —$OR^{10}$, —$SR^{10}$, —$N(R^7)_2$, —$N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_2$-$C_6$ cycloalkoxy, —$NO_2$, —CN, —$CF_3$, —$SO_2(C_1$-$C_6$ alkyl), —$NR^{10}SO_2R^6$—$SO_2N(R^6)_2$, —S(O)($C_1$-$C_6$ alkyl), —$NHCOOR^6$, —$NHCOR^6$, —$NHCONHR^6$, —$CO_2R^{10}$, —$C(O)R^{10}$, and —$CON(R^{10})_2$; wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^6$ is $C_1$-$C_8$ alkyl, $C_3$-$C_8$ cycloalkyl, $C_3$-$C_8$ cycloalkyl($C_1$-$C_5$)alkyl, aryl, aryl($C_1$-$C_4$)alkyl, heteroaryl, heteroaryl ($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W' substituents or aryl is substituted by —$P(O)R^{11}R^{12}$; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Y is —C(═O)—, —$SO_2$—, or —C(═N—CN)—;

Z is)-$C(R^{10})_2$—, —O—, or —$N(R^4)$—;

M is $C_1$-$C_{12}$ alkylene or $C_2$-$C_{12}$ alkenylene or $C_2$-$C_{12}$ alkynylene, wherein said alkylene or alkenylene is optionally substituted with 1, 2 or 3 substituents selected from the group consisting of $C_1$-$C_8$ alkyl, $C_3$-$C_8$ cycloalkyl ($C_1$-$C_8$ alkyl), and aryl($C_1$-$C_8$ alkyl); wherein 2 substituents on adjacent carbon atoms of M are optionally taken together to form a 3- to 6-membered cyclic ring containing 0 to 3 heteroatoms selected from N, O and S, or 2 substituents on the same carbon atom of M are optionally taken together to form a 3- to 6-membered cyclic ring containing 0 to 3 heteroatoms selected from N, O and S;

A is —$C(R^{16})$— or —N—;

when $R^5$ is other than H, $R^{16}$ is H, $C_1$-$C_6$ alkyl, halo, —$OR^{10}$, —$SR^{10}$, or —$N(R^{10})_2$;

when $R^5$ is H, $R^{16}$ is H, $C_1$-$C_6$ alkyl, halo, —OH, $C_1$-$C_6$ alkoxy, —CN, —$CF_3$, —$SR^{10}$, —$SO_2(C_1$-$C_6$ alkyl), $C_3$-$C_8$ cycloalkyl, $C_3$-$C_8$ cycloalkoxy, $C_1$-$C_6$ haloalkyl, —$N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, —$OR^{10}$, —$SR^{10}$, —$N(R^7)_2$, —$N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_1$-$C_6$ cycloalkoxy, —$NO_2$, —CN, —$CF_3$, —$SO_2(C_1$-$C_6$ alkyl), —$NR^{10}SO_2R^6$—$SO_2N$ $(R^6)_2$, —S(O)($C_1$-$C_6$ alkyl), —$NHCOOR^6$, —$NHCOR^6$, —$NHCONHR^6$, —$CO_2R^{10}$, —$C(O)R^{10}$, and —$CON(R^{10})_2$; wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

or $R^5$ and $R^{16}$ are optionally taken together to form a 5- to 6-membered saturated, unsaturated non-aromatic, or aromatic cyclic ring having 0 to 2 heteroatoms selected from N, O and S;

each $R^7$ is independently H, $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W' substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently H, halo, —$OR^7$, $C_1$-$C_6$ alkyl, —CN, —$CF_3$ —$SR^7$, —$CO_2R^7$, —$CON(R^7)_2$, —C(O) $R^7$, —$N(R^{10})C(O)R^7$, —$SO_2(C_1$-$C_6$ alkyl), —S(O)($C_1$-$C_6$ alkyl), $C_3$-$C_8$ cycloalkyl, $C_3$-$C_8$ cycloalkoxy, $C_1$-$C_6$ haloalkyl, —$N(R^7)_7$, —$N(C_1$-$C_6$ alkyl)$O(C_1$-$C_6$ alkyl), halo($C_1$-$C_6$ alkoxy), —$NR^{10}SO_2R^7$, —$SO_2N(R^7)_2$, —$NHCOOR^7$, —$NHCONHR^7$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein 2 adjacent W moieties are optionally taken together with the atoms to which they are attached to form a 5- to 6-membered saturated, unsaturated non-aromatic, or aromatic cyclic ring having 0 to 2 heteroatoms selected from N, O and S;

each W' is independently H, halo, —$OR^{10}$, $C_1$-$C_6$ alkyl, —CN, —$NO_2$, —$SR^{10}$, —$CO_2R^{10}$, —$CON(R^{10})_2$, —$C(O)R^{10}$, —$N(R^{10})C(O)R^{10}$, —$SO_2(C_1$-$C_6$ alkyl), —S(O)($C_1$-$C_{1-6}$ alkyl), $C_3$-$C_8$ cycloalkyl, $C_3$-$C_8$ cycloalkoxy, $C_1$-$C_6$ haloalkyl, —$N(R^{10})_2$ —$N(C_1$-$C_6$ alkyl)$O(C_1$-$C_6$ alkyl), halo($C_1$-$C_6$ alkoxy), —$NR^{10}SO_2R^{10}$, —$SO_2N(R^{10})_2$, —$NHCOOR^{10}$, —$NHCONHR^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein 2 adjacent W' moieties are optionally taken together with the atoms to which they are attached to form a 5- to 6-membered saturated, unsaturated non-aromatic, or aromatic cyclic ring having 0 to 2 heteroatoms selected from N, O and S;

each $R^{10}$ is independently H or $C_1$-$C_6$ alkyl;

each $R^{11}$ is independently $C_1$-$C_6$ alkyl, —$OR^{13}$, —$N(R^{10}$-V-$CO_2R^{10}$, —O-V-$CO_2R^{10}$, —S-V-$CO_2R^{10}$, —$N(R^{10})$ $(R^{13})$, $R^{14}$, or —$N(R^{10})SO_2R^6$;

each $R^{12}$ is independently —$OR^{13}$, —$N(R^{10})$-V-$CO_2R^{10}$, —O-V-$CO_2R^{10}$, —S-V-$CO_2R^{10}$, or —$N(R^{10})(R^{13})$;

or $R^{11}$ and $R^{12}$ are optionally taken together, with the phosphorus atom to which they are attached, to form a 5- to 7-membered monocyclic ring;

each V is independently —CH($R^{15}$) or $C_1$-$C_4$ alkylene-CH ($R^{15}$);

each $R^{13}$ is independently H, $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of aryl, aryl ($C_1$-$C_4$ alkyl), $C_3$-$C_8$ cycloalkyl, $C_3$-$C_8$ cycloalkyl($C_1$-$C_4$ alkyl), heteroaryl, heteroaryl($C_1$-$C_4$ alkyl), heterocyclyl, heterocyclyl($C_1$-$C_4$ alkyl), $C_1$-$C_6$ alkyl, halo, —OC(O)OR$^6$, —OC(O)R$^6$, —OR$^{10}$, —SR$^{10}$, —N($R^{10}$)$_2$, C(O)R$^{10}$, —$NO_2$, —CN, —$CF_3$, —$SO_2$($C_1$-$C_6$ alkyl), —S(O)($C_1$-$C_6$ alkyl), —NR$^{10}$SO$_2$R$^6$, —SO$_2$N($R^6$)$_2$, —NHCOOR$^6$, —NHCOR$^6$, —NHCONHR$^6$, —CO$_2$R$^{10}$, and —C(O)N($R^{10}$)$_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^{14}$ is $C_1$-$C_6$ alkyl, $C_2$-$C_6$ alkenyl, aryl or heteroaryl, wherein aryl is phenyl or naphthyl, and heteroaryl is independently a 5- or 6-membered aromatic ring having 1, 2 or 3 heteroatoms selected from N, O and S, attached through a ring carbon or nitrogen, and wherein said aryl or heteroaryl is optionally substituted with 1 to 2 substituents selected from the group consisting of $C_1$-$C_6$ alkyl, halo, —OC(O)OR$^6$, —OC(O)R$^6$, —OR$^{10}$, —SR$^{10}$, —N($R^{10}$)$_2$, —C(O)R$^{10}$, —$NO_2$—CN, —$CF_3$, —$SO_2$($C_1$-$C_6$ alkyl), —S(O)($C_1$-$C_6$ alkyl), —NR$^{10}$SO$_7$R$^6$—SO$_2$N($R^6$)$_2$, —NHCOOR$^6$, —NHCOR$^6$, —NHCONHR$^6$, —CO$_2$R$^{10}$, and —C(O)N($R^{10}$)$_2$; and each $R^{15}$ is independently $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of $C_1$-$C_6$ alkyl, halo, —OC(O)OR$^6$, —OC(O)R$^6$, —OR$^{10}$, —SR$^{10}$, —N($R^{10}$)$_2$, —C(O)R$^{10}$, —$NO_2$, —CN, —$CF_3$, —$SO_2$($C_1$-$C_6$ alkyl), —S(O)($C_1$-$C_6$ alkyl), —NR$^{10}$SO$_2$R$^6$, —SO$_2$N($R^6$)$_2$, —NHCOOR$^6$, —NHCOR$^6$, —NHCONHR$^6$, —CO$_2$R$^{10}$, and —C(O)N($R^{10}$)$_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S.

21. A method of inhibiting HCV NS3 protease in a subject in need thereof, said method comprising administering to the subject an effective amount of a compound of formula (I):

(I)

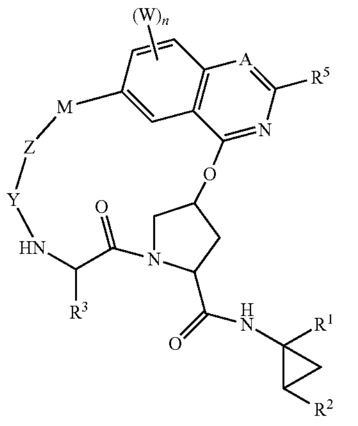

or a pharmaceutically acceptable salt thereof, wherein:

n is 1 or 2;

$R^1$ is —CONHP(O)R$^{11}$R$^{12}$, or —P(O)R$^{11}$R$^{12}$;

$R^2$ is $C_1$-$C_6$ alkyl, $C_2$-$C_6$ alkenyl or $C_3$-$C_8$ cycloalkyl, wherein said alkyl, alkenyl or cycloalkyl is optionally substituted with 1 to 3 halo;

$R^3$ is $C_1$-$C_8$ alkyl, $C_3$-$C_8$ cycloalkyl, $C_3$-$C_8$ cycloalkyl($C_1$-$C_8$)alkyl, aryl($C_1$-$C_8$)alkyl, or Het, wherein aryl is phenyl or naphthyl and said alkyl, cycloalkyl, or aryl is optionally substituted with 1 to 3 substituents selected from the group consisting of halo, —OR$^{10}$, —SR$^{10}$, —N($R^{10}$)$_2$, —N($C_1$-$C_6$ alkyl)O($C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2$($C_1$-$C_6$ alkyl), —S(O)($C_1$-$C_6$ alkyl), —NR$^{10}$SO$_2$R$^6$, —SO$_2$N($R^6$)$_2$, —NHCOOR$^6$, —NHCOR$^6$, —NHCONHR$^6$, —CO$_2$R$^{10}$, —C(O)R$^{10}$, and —CON($R^{10}$)$_2$; Het is a 5- to 6-membered saturated cyclic ring having 1, 2 or 3 heteroatoms selected from N, O and S, wherein said ring is optionally substituted with 1 to 3 substituents selected from the group consisting of halo, —OR$^{10}$, —SR$^{10}$, —N($R^{10}$)$_2$, —N($C_1$-$C_6$ alkyl)O ($C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2$($C_1$-$C_6$ alkyl), —S(O)($C_1$-$C_6$ alkyl), —NR$^{10}$SO$_2$R$^6$, —SO$_2$N($R^6$)$_2$, —NHCOOR$^6$, —NHCOR$^6$, —NHCONHR$^6$, —CO$_2$R$^{10}$, —C(O)R$^{10}$, and)-CON($R^{10}$)$_2$;

$R^4$ is H, $C_1$-$C_8$ alkyl, $C_3$-$C_8$ cycloalkyl($C_1$-$C_8$)alkyl, or aryl ($C_1$-$C_8$)alkyl; wherein aryl is phenyl or naphthyl and said alkyl, cycloalkyl, or aryl is optionally substituted with 1 to 3 substituents selected from the group consisting of halo, —OR$^{10}$, —SR$^{10}$, —N($R^{10}$)$_2$, —N($C_1$-$C_6$ alkyl)O($C_1$-$C_6$ alkyl), $C_1$-$C_6$ alkyl, $C_1$-$C_6$ haloalkyl, halo ($C_1$-$C_6$ alkoxy), —$NO_2$, —CN, —$CF_3$, —$SO_2$($C_1$-$C_6$ alkyl), —S(O)($C_1$-$C_6$ alkyl), —NR$^{10}$SO$_2$R$^6$, —SO$_2$N ($R^6$)$_2$, —NHCOOR$^6$, —NHCOR$^6$, —NHCONHR$^6$, —CO$_2$R$^{10}$, —C(O)R$^{10}$, and —CON($R_{10}$)$_2$;

$R^5$ is H, halo, —OH, $C_1$-$C_6$ alkoxy, $C_1$-$C_6$ alkyl, —CN, —$CF_3$, —SR$^{10}$, —$SO_2$($C_1$-$C_6$ alkyl), $C_3$-$C_8$ cycloalkyl, $C_3$-$C_8$ cycloalkoxy, $C_1$-$C_6$ haloalkyl, —N($R^7$)$_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, —$OR^{10}$, —$SR^{10}$, —$N(R^7)_2$, —$N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, —$NO_2$, —CN, —$CF_3$, —$SO_2(C_1$-$C_6$ alkyl), —$NR^{10}SO_2R^6$, —$SO_2N(R^6)_2$, —$S(O)(C_1$-$C_6$ alkyl), —$NHCOOR^6$, —$NHCOR^6$, —$NHCONHR^6$, —$CO_2R^{10}$, —$C(O)R^{10}$, and —$CON(R^{10})_2$; wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^6$ is $C_1$-$C_8$ alkyl, $C_3$-$C_8$ cycloalkyl, $C_3$-$C_8$ cycloalkyl($C_1$-$C_5$)alkyl, aryl, aryl($C_1$-$C_4$)alkyl, heteroaryl, heteroaryl ($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W' substituents or aryl is substituted by —$P(O)R^{11}R^{12}$; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Y is —C(═O)—, —$SO_2$—, or —C(═N—CN)—;

Z is —$C(R^{10})_2$—, —O—, or —$N(R^4)$—;

M is $C_1$-$C_{12}$ alkylene or $C_2$-$C_{12}$ alkenylene or $C_2$-$C_{12}$ alkynylene, wherein said alkylene or alkenylene is optionally substituted with 1, 2 or 3 substituents selected from the group consisting of $C_1$-$C_8$ alkyl, $C_3$-$C_8$ cycloalkyl ($C_1$-$C_8$ alkyl), and aryl($C_1$-$C_8$ alkyl); wherein 2 substituents on adjacent carbon atoms of M are optionally taken together to form a 3- to 6-membered cyclic ring containing 0 to 3 heteroatoms selected from N, O and S, or 2 substituents on the same carbon atom of M are optionally taken together to form a 3- to 6-membered cyclic ring containing 0 to 3 heteroatoms selected from N, O and S;

A is —$C(R^{16})$— or —N—;

when $R^5$ is other than H, $R^{16}$ is H, $C_1$-$C_6$ alkyl, halo, —$OR^{10}$, —$SR^{10}$, or —$N(R^{10})_2$;

when $R^5$ is H, $R^{16}$ is H, $C_1$-$C_6$ alkyl, halo, —OH, $C_1$-$C_6$ alkoxy, —CN, —$CF_3$, —$SR^{10}$, —$SO_2(C_1$-$C_6$ alkyl), $C_3$-$C_8$ cycloalkyl, $C_3$-$C_8$ cycloalkoxy, $C_1$-$C_6$ haloalkyl, —$N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, —$OR^{10}$, —$SR^{10}$, —$N(R^7)_2$, —$N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, —$NO_2$, —CN, —$CF_3$, —$SO_2(C_1$-$C_6$ alkyl), —$NR^{10}SO_2R^6$, —$SO_2N(R^6)_2$, —$S(O)(C_1$-$C_6$ alkyl), —$NHCOOR^6$, —$NHCOR^6$, —$NHCONHR^6$, —$CO_2R^{10}$, —$C(O)R^{10}$, and —$CON(R^{10})_2$; wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

or $R^5$ and $R^{16}$ are optionally taken together to form a 5- to 6-membered saturated, unsaturated non-aromatic, or aromatic cyclic ring having 0 to 2 heteroatoms selected from N, O and S;

each $R^7$ is independently H, $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W' substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently H, halo, —$OR^7$, $C_1$-$C_6$ alkyl, —CN, —$CF_3$, —$NO_2$, —$SR^7$, —$CO_2R^7$, —$CON(R^7)_2$, —$C(O)R^7$, —$N(R^{10})C(O)R^7$, —$SO_2(C_1$-$C_6$ alkyl), —$S(O)(C_1$-$C_6$ alkyl), $C_3$-$C_8$ cycloalkyl, $C_3$-$C_8$ cycloalkoxy, $C_1$-$C_6$ haloalkyl, —$N(R^7)_2$, —$N(C_1$-$C_6$ alkyl)$O(C_1$-$C_6$ alkyl), halo($C_1$-$C_6$ alkoxy), —$NR^{10}SO_2R^7$, —$SO_2N(R^7)_2$, —$NHCOOR^7$, —$NHCONHR^7$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein 2 adjacent W moieties are optionally taken together with the atoms to which they are attached to form a 5- to 6-membered saturated, unsaturated non-aromatic, or aromatic cyclic ring having 0 to 2 heteroatoms selected from N, O and S;

each W' is independently H, halo, —$OR^{10}$, $C_1$-$C_6$ alkyl, —CN, —$CF_3$, —$NO_2$, —$SR^{10}$, —$CO_2R^{10}$, —$CON(R^{10})_2$, —$C(O)R^{10}$, —$N(R^{10})C(O)R^{10}$, —$SO_2$ ($C_1$-$C_6$ alkyl), —$S(O)(C_1$-$C_6$ alkyl), $C_3$-$C_8$ cycloalkyl, $C_3$-$C_8$ cycloalkoxy, $C_1$-$C_6$ haloalkyl, —$N(R^{10})_2$, —$N(C_1$-$C_6$ alkyl)$O(C_1$-$C_6$ alkyl), halo($C_1$-$C_6$ alkoxy), —$NR^{10}SO_2R^{10}$, —$SO_2N(R^{10})_2$, —$NHCOOR^{10}$, —$NHCONHR^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein 2 adjacent W' moieties are optionally taken together with the atoms to which they are attached to form a 5- to 6-membered saturated, unsaturated non-aromatic, or aromatic cyclic ring having 0 to 2 heteroatoms selected from N, O and S;

each $R^{10}$ is independently H or $C_1$-$C_6$ alkyl;

each $R^{11}$ is independently $C_1$-$C_6$ alkyl, —$OR^{13}$, —$N(R^{10}$-V-$CO_2R^{10}$, —O-V-$CO_2R^{10}$, —S-V-$CO_2R^{10}$, —$N(R^{10})(R^{13})$, —$N(R^{10})SO_2R^6$;

each $R^{12}$ is independently —$OR^{13}$, —$N(R^{10})$-V-$CO_2R^{10}$, —O-V-$CO_2R^{10}$, —S-V-$CO_2R^{10}$, or —$N(R^{10})(R^{13})$;

or $R^{11}$ and $R^{12}$ are optionally taken together, with the phosphorus atom to which they are attached, to form a 5- to 7-membered monocyclic ring;

each V is independently —$CH(R^{15})$ or $C_1$-$C_4$ alkylene-CH ($R^{15}$);

each $R^{13}$ is independently H, $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of aryl, aryl ($C_1$-$C_4$ alkyl), $C_3$-$C_8$ cycloalkyl, $C_3$-$C_8$ cycloalkyl($C_1$-$C_4$ alkyl), heteroaryl, heteroaryl($C_1$-$C_4$ alkyl), heterocyclyl, heterocyclyl($C_1$-$C_4$ alkyl), $C_1$-$C_6$ alkyl, halo, —$OC(O)OR^6$, —$OC(O)R^6$, —$OR^{10}$, —$SR^{10}$, —$N(R^{10})_2$, —$C(O)R^{10}$, —$NO_2$, —CN, —$CF_3$, —$SO_2$ ($C_1$-$C_6$ alkyl), —S(O)($C_1$-$C_6$ alkyl), —$NR^{10}SO_2R^6$, —$SO_2N(R^6)_2$, —$NHCOOR^6$, —$NHCOR^6$, —NH-$CONHR^6$, —$CO_2R^{10}$, and —$C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^{14}$ is $C_1$-$C_6$ alkyl, $C_2$-$C_6$ alkenyl, aryl or heteroaryl, wherein aryl is phenyl or naphthyl, and heteroaryl is independently a 5- or 6-membered aromatic ring having 1, 2 or 3 heteroatoms selected from N, O and S, attached through a ring carbon or nitrogen, and wherein said aryl or heteroaryl is optionally substituted with 1 to 2 substituents selected from the group consisting of $C_1$-$C_6$ alkyl, halo, —$OC(O)OR^6$, —$OC(O)R^6$, —$OR^{10}$, —$SR^{10}$, —$N(R^{10})_2$, —$C(O)R^{10}$, —$NO_2$, —CN, —$CF_3$, —$SO_2$($C_1$-$C_6$ alkyl), —S(O)($C_1$-$C_6$ alkyl), —$NR^{10}SO_2R^6$, —$SO_2N(R^6)_2$, —$NHCOOR^6$, —NH-$COR^6$, —$NHCONHR^6$, —$CO_2R^{10}$, and —$C(O)N(R^{10})_2$; and each $R^{15}$ is independently $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of $C_1$-$C_6$ alkyl, halo, —$OC(O)OR^6$, —$OC(O)R^6$, —$OR^{10}$, —$SR^{10}$, —$N(R^{10})_2$, —$C(O)R^{10}$, —$NO_2$, —CN, —$CF_3$, —$SO_2$($C_1$-$C_6$ alkyl), —S(O)($C_1$-$C_6$ alkyl), —$NR^{10}SO_2R^6$, —$SO_2N(R^6)_2$, —$NHCOOR^6$, —NH-$COR^6$, —$NHCONHR^6$, —$CO_2R^{10}$, and —$C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S.

* * * * *